(12) United States Patent
Fujisawa et al.

(10) Patent No.: US 9,720,140 B2
(45) Date of Patent: Aug. 1, 2017

(54) OPTICAL FILM, CIRCULARLY POLARIZING PLATE AND ORGANIC ELECTROLUMINESCENT DISPLAY DEVICE

(71) Applicant: KONICA MINOLTA, INC., Chiyoda-ku, Tokyo (JP)

(72) Inventors: Rie Fujisawa, Ebina (JP); Hiroyoshi Kiuchi, Hachioji (JP); Kiyoshi Fukusaka, Fussa (JP); Takatugu Suzuki, Hachiohi (JP); Hiroshi Kita, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/785,774

(22) PCT Filed: Apr. 16, 2014

(86) PCT No.: PCT/JP2014/060808
§ 371 (c)(1),
(2) Date: Oct. 20, 2015

(87) PCT Pub. No.: WO2014/175136
PCT Pub. Date: Oct. 30, 2014

(65) Prior Publication Data
US 2016/0070030 A1    Mar. 10, 2016

(30) Foreign Application Priority Data

Apr. 23, 2013  (JP) .................................. 2013-089929

(51) Int. Cl.
*G02B 1/08*     (2006.01)
*G02B 5/30*     (2006.01)
(Continued)

(52) U.S. Cl.
CPC ................ *G02B 1/08* (2013.01); *C07C 69/86* (2013.01); *C07C 235/56* (2013.01);
(Continued)

(58) Field of Classification Search
CPC ...... G02B 1/08; G02B 5/3083; C07C 233/80; C07D 213/69; C07D 231/12;
(Continued)

(56) References Cited

U.S. PATENT DOCUMENTS 6,013,331 A * 1/2000 Ogawa .................... B05D 1/185
                                                     427/352
6,060,183 A * 5/2000 Higashi ................ G02B 5/3083
                                                       349/117

(Continued)

FOREIGN PATENT DOCUMENTS

JP          05140045 A       6/1993
JP          07207169 A       8/1995
(Continued)

OTHER PUBLICATIONS

J.H.G Rangel et al., "Study on the orientation degree of Pb(1-x)LaxTiO3 thin films by the rocking curve technique and its morphological aspects", Surface & Coatings Technology, 201, Jan. 12, 2007, pp. 6345-6351.*

(Continued)

*Primary Examiner* — Frank Font
(74) *Attorney, Agent, or Firm* — Holtz, Holtz & Volek PC

(57) ABSTRACT

Provided is an optical film containing a cellulose derivative, the optical film having an in-plane retardation $Ro_{550}$ within the range of 120 to 160 nm measured at a wavelength of 550 nm under an atmosphere of a temperature of 23° C. and a relative humidity of 55%, and a ratio $Ro_{450}/Ro_{550}$ within the range of 0.65 to 0.99, $Ro_{450}/Ro_{550}$ being a ratio of an in-plane retardation $Ro_{450}$ measured at a wavelength of 450

(Continued)

nm to the in-plane retardation $Ro_{550}$ measured at a wavelength of 550 nm, wherein, a substituent of a glucose skeleton in the cellulose derivative satisfies the requirements (a) and (b) which are described in the specification, and the optical film contains a compound A satisfying the following condition defined by Expression (a1) which is described in the specification.

11 Claims, 6 Drawing Sheets

(51) Int. Cl.
| | |
|---|---|
| C07D 231/12 | (2006.01) |
| C07D 249/08 | (2006.01) |
| C07D 271/06 | (2006.01) |
| C08B 13/00 | (2006.01) |
| C07D 213/69 | (2006.01) |
| C07C 235/56 | (2006.01) |
| C07C 69/86 | (2006.01) |
| C08K 5/20 | (2006.01) |
| C08K 5/3432 | (2006.01) |
| C08K 5/3445 | (2006.01) |
| C08K 5/3472 | (2006.01) |
| C08K 5/353 | (2006.01) |
| H01L 51/52 | (2006.01) |
| H05B 33/02 | (2006.01) |

(52) U.S. Cl.
CPC ......... *C07D 213/69* (2013.01); *C07D 231/12* (2013.01); *C07D 249/08* (2013.01); *C07D 271/06* (2013.01); *C08B 13/00* (2013.01); *C08K 5/20* (2013.01); *C08K 5/3432* (2013.01); *C08K 5/3445* (2013.01); *C08K 5/3472* (2013.01); *C08K 5/353* (2013.01); *G02B 5/3025* (2013.01); *G02B 5/3083* (2013.01); *H01L 51/5281* (2013.01); *H05B 33/02* (2013.01)

(58) Field of Classification Search
CPC ...... C07D 249/08; C07D 271/06; C08B 3/16; C08B 13/00; C08K 5/3432; C08K 5/3445; C08K 5/3472; C08K 5/353; C08L 1/08; H01L 51/50; H05B 33/02; G02F 1/1335; H01J 5/16
USPC ...... 359/489.07; 349/117, 121, 181; 313/112
See application file for complete search history.

(56) References Cited

U.S. PATENT DOCUMENTS

| | | | |
|---|---|---|---|
| 6,565,974 B1 | 5/2003 | Uchiyama et al. | |
| 8,282,864 B2* | 10/2012 | Umemoto | C07D 295/02 252/585 |
| 2006/0066011 A1* | 3/2006 | Oya | C08B 3/06 264/330 |
| 2007/0290168 A1* | 12/2007 | Fukagawa | C09K 19/18 252/299.01 |
| 2008/0049323 A1* | 2/2008 | Sugiyama | B29D 11/0074 359/489.02 |
| 2008/0107829 A1 | 5/2008 | Oya et al. | |
| 2008/0241430 A1* | 10/2008 | Imai | C08B 3/16 428/1.5 |
| 2008/0284957 A1* | 11/2008 | Haruta | C08K 5/10 349/117 |
| 2009/0027599 A1* | 1/2009 | Ohgaru | C08K 5/10 349/96 |
| 2009/0043088 A1* | 2/2009 | Shimamoto | C08B 3/00 536/58 |
| 2009/0092771 A1* | 4/2009 | Sasata | C08L 1/10 428/1.31 |
| 2009/0142516 A1* | 6/2009 | Sasada | C08B 3/06 428/1.31 |
| 2009/0225262 A1* | 9/2009 | Yanai | C09K 19/3068 349/119 |
| 2009/0247739 A1* | 10/2009 | Nozoe | C07H 7/02 536/123.1 |
| 2009/0290100 A1* | 11/2009 | Haruta | C08J 5/18 349/75 |
| 2010/0009067 A1* | 1/2010 | Inoue | G02B 5/3016 427/66 |
| 2010/0020273 A1* | 1/2010 | Toyama | G02F 1/13363 349/96 |
| 2010/0142050 A1* | 6/2010 | Suzuki | G02F 1/0136 359/487.02 |
| 2011/0070363 A1* | 3/2011 | Komatsubara | C08J 7/12 427/163.1 |
| 2011/0076423 A1 | 3/2011 | Nagura et al. | |
| 2011/0262661 A1 | 10/2011 | Nagura et al. | |
| 2013/0128359 A1* | 5/2013 | Wakita | G02B 5/30 359/489.07 |

FOREIGN PATENT DOCUMENTS

| | | |
|---|---|---|
| JP | 08321381 A | 12/1996 |
| JP | 10068816 A | 3/1998 |
| JP | 2005154342 A | 6/2005 |
| JP | 2006091807 A | 4/2006 |
| JP | 2007047537 A | 2/2007 |
| JP | 2008095026 A | 4/2008 |
| JP | 2011094114 A | 5/2011 |
| JP | 2011227508 A | 11/2011 |
| JP | 2011241379 A | 12/2011 |
| JP | 2012215817 A | 11/2012 |
| JP | 2013024903 A | 2/2013 |
| WO | 0026705 A1 | 5/2000 |
| WO | 2014050578 A1 | 4/2014 |

OTHER PUBLICATIONS

International Search Report (ISR) dated Jul. 15, 2014 issued in International Application No. PCT/JP2014/060808.
International Preliminary Report on Patentability (IPRP) including Written Opinion (and English translation thereof) dated Oct. 27, 2015, issued in parent International Application No. PCT/JP2014/060808.

* cited by examiner

OPTICAL FILM, CIRCULARLY POLARIZING PLATE AND ORGANIC ELECTROLUMINESCENT DISPLAY DEVICE

TECHNICAL FIELD

The present invention relates to an optical film that retards the phase of wide-band visible light by λ/4 and maintains stable performance in various environments of usage, and to a circularly polarizing plate and an organic electroluminescent display device, each including the optical film.

BACKGROUND

Liquid crystal display devices, which are common display devices, are required to have high display performance and durability and expected to display images in excellent contrast and tone balance at a wide viewing angle. Such requirements have been met through the use of liquid crystal panels conforming to various display modes for liquid crystal display devices, for example, the VA (vertical alignment) mode, the OCB (optically compensated bend) mode, and the IPS (in-plane switching) mode. Such liquid crystal panels have wider viewing angles and higher display performance compared to those of liquid crystal panels conforming to the conventional TN (twisted nematic) mode.

Along with the increasing demand for energy efficiency, there also has been an increasing demand for display devices with wide viewing angles and high display performance. In such view, display devices including organic electroluminescent (hereafter, it is abbreviated as an organic EL) backlights have been drawing attention as next-generation display devices conforming to a new display mode.

An organic EL display device includes pixels provided with light sources that can be independently turned on or off. Thus, power consumption is low compared to that of liquid crystal display devices, which include backlights that are always turned on during image display. The control of transmission and non-transmission of light through each pixel in an image displayed on liquid crystal display devices involves a liquid crystal cell and polarizing plate disposed on both sides of the liquid crystal cell; whereas organic EL display devices do not require such a configuration because images can be formed through turning on and off the light sources, and thus can have significantly sharp front contrast and a wide viewing angle. In particular, the use of organic EL elements of the colors blue (B), green (G), and red (R) eliminates the need for color filters, which are essential for liquid crystal display devices; thus, organic EL display devices are expected to achieve higher contrast.

A typical organic EL display device includes a reflector having a mirror surface on the surface opposite to the light-extracting surface in the form of a highly reflective metal material serving as an electrode layer constituting the cathode or a separate metal plate serving as a reflector, to efficiently transmit light from a light-emitting layer to the viewed surface.

Unfortunately, unlike liquid crystal display devices, organic EL display devices do not include crossed Nicol polarizers; thus, external light is reflected by the light-extracting reflectors and forms a reflection, causing a significant decrease in contrast in a high brightness environment.

To solve such a problem, for example, a countermeasure is disclosed involving a circularly polarizer element for prevention of reflection of external light by a mirror surface (for example, refer to Patent Document 1). The circularly polarizer element described in Patent Document 1 includes an absorptive linear polarizing plate and a λ/4 retarder film, which are laminated such that their optical axes intersect at 45° or 135°.

A conventional retarder can adjust the retardation of a monochrome light beam to λ/4 or λ/2 of the wavelength of the light beam, but converts white light, which consists of combined waves of various visible light beams, into a spectrum of colored light polarized in accordance with the different wavelengths. This is because the material of the retarder exhibits wavelength dispersion corresponding to the phase difference.

To solve such a problem, various wideband retarders have been studied to achieve uniform retardation of light beams over a wide wavelength band. For example, a retarder includes a λ/4 wave plate that retards birefringent light by ¼ of the wavelength and a λ/2 wave plate that retards birefringent light by ½ of the wavelength, which are bonded together such that their optical axes intersect (for example, refer to Patent Document 2).

The production of the retarders described above requires a complicated step of adjusting the optical direction (optical axis or slow axis) of two polymeric films and a step of bonding multiple films with an adhesive layer, which hinders the advantage of organic EL display devices of being thin; thus, there is a need for the development of a wideband λ/4 retarder having a non-laminated single layer configuration.

Similar to the liquid crystal display device, an absorptive linear polarizing plate in a circularly polarizing plate described above is typically composed of polyvinyl alcohol (hereafter, it is abbreviated as PVA) containing dichroic pigments and stretched to a length much greater than the original length; such a polarizer film is readily affected by the external environment, and thus requires a protective film. A widely used protective film for polarizer elements is composed of cellulose, for example, cellulose ester, which has excellent adhesiveness to PVA in the form of a polarizer element and high total light transmittance. Thus, the polarizing plate includes a polarizer element and polarizer protective films disposed on both sides of the polarizer element, and must also include a λ/4 retarder film so as to function as a circularly polarizing plate.

The λ/4 retarder film disposed on the polarizing plate protective film causes the retardation to deviate from λ/4, which is a desired optical property, due to the slight retardation ability of the polarizer protective film, and the increased number of components causes an increase in the thickness; thus, there is a demand for the development of an optical film that can function as both a polarizer protective film and a wideband λ/4 retarder.

A technique for producing a monolayer wideband λ/4 retarder film is disclosed. The λ/4 retarder film is produced through uniaxial stretching of a copolymer film composed of polymerized monomers having positive refractive-index anisotropy and monomers having negative birefringence (for example, refer to Patent Document 3). The uniaxially stretched polymeric film has inverse wavelength dispersion, which enables the production of a wideband λ/4 retarder from a single retarder film. Unfortunately, the polarizing plate protective film has poor adhesiveness to a polarizer element and insufficient total light transmittance.

The application of an optical film functioning both as an optical compensator and a polarizing plate protective film to a liquid crystal display device has been investigated. As such a film, an optical film consisting of a cellulose ester film having a predetermined retardation has been studied. For example, an optical film in the form of a retarder film conforming to the VA mode is disclosed. The retarder film is composed of cellulose ester having an in-plane retardation Ro of approximately 50 nm and a retardation Rt across the thickness of approximately 130 nm (for example, refer to Patent Document 4).

Cellulose ester is characterized in that a decrease in the degree of substitution relatively increases the phase difference but decreases the inverse wavelength dispersion, whereas an increase in the degree of substitution increases the inverse wavelength dispersion but decreases the retardation. Thus, a monolayer wideband λ/4 retarder can only be produced with a large thickness.

Other techniques have been investigated for an enhancement in the retardation and the wavelength dispersion of a film through the addition of additives, such as retardation enhancers and wavelength dispersion adjusters, to cellulose esters. Unfortunately, a large amount of additives impairs the quality of the film, causing a decrease in durability and transparency; thus, a solution to this drawback is required.

To solve the issues described above, a technique has been studied for the enhancement in the wavelength dispersion of a cellulose ester film through introduction of specific aromatic ester groups to cellulose ester (for example, refer to Patent Document 5). The technique proposed in Patent Document 5 can freely control the wavelength dispersion of a cellulose ester film without causing a decrease in the retardation ability.

The present inventors have conducted an extensive study on the technique proposed in Patent Document 5 and have identified a problem of unevenness in tone and reflection of displayed images that occurs depending on the use environment when a wideband λ/4 retarder film is used as a circularly polarizing plate for an organic EL display device, which is produced through control of the substituents of cellulose ester described in Patent Document 5 so as to adjust retardation and wavelength dispersibility corresponding to phase difference.

Accompanied by the introduction of a thinner thickness of an organic EL display device, the employing environment thereof has been enlarged and the applications thereof have been diversified. It was found that an organic EL display device was particularly prone to the problem described above when humidity fluctuated in the use environment; thus, the need for immediate measures for improvement was apparent.

Further, it was found that a cellulose ester film had a high hygroscopic property and had a large variation of retardation value according to the change of environmental humidity. With respect to this problem, it has been examined a method of decreasing the change of the optical property which depends on the environmental humidity by incorporating a specific additive in a cellulose ester film.

Patent Document 6 discloses a method using a cellulose ester film which incorporates a compound having a value obtained by dividing a molecular weight with a sum of a hydrogen bond donor number and a hydrogen bond acceptor number in the specific range.

Patent Document 7 discloses an example of adding a benzoic acid derivative, and Patent Document 8 discloses an example of adding a nucleic acid derivative to a cellulose ester film as a humidity resistance improving agent.

Patent Document 9 discloses a method using a cellulose ester film which incorporates a high moisture absorptive compound having a water content difference of 2% or more.

The present inventors examined the methods each described in Patent Documents 6 to 9 under the severer environmental conditions than before. It was found that although the methods described in Patent Documents 6 to 9 showed certain improvement under mild environmental conditions, the durability was still insufficient for the purpose of using for a high-grade display device recently developed, and that further improvement was still required.

That is, the film may be under the severe environment such as directly exposed to water by dew condensation during transportation of the film. Even in this environment, it has become required a property of showing no property variation. It was found that the known methods described in Patent Documents 6 to 9 showed only small improvement effect under the severe conditions such as directly exposed to water as described above.

PRIOR ART DOCUMENTS

Patent Documents

Patent Document 1: Japanese Patent Application Publication (JP-A) No. 8-321381
Patent Document 2: JP-A No. 10-68816
Patent Document 3: WO 2000/026705
Patent Document 4: JP-A No. 2007-47537
Patent Document 5: JP-A No. 2008-95026
Patent Document 6: JP-A No. 2011-094114
Patent Document 7: JP-A No. 2011-227508
Patent Document 8: JP-A No. 2011-241379
Patent Document 9: JP-A No. 2012-215817

SUMMARY OF THE INVENTION

Problems to be Solved by the Invention

An object of the present invention, which has been conceived in light of the problems described above, is to provide an optical film of a circularly polarizing plate, which serves as an antireflective layer in an organic electroluminescent display device, that can retard visible light in a wide range by substantially λ/4, exhibits a reduced variation in optical performance under variable humidity, and functions as a protective film for a polarizing plate; a circularly polarizing plate including the optical film; and an organic electroluminescent display device including the circularly polarizing plate as an antireflective component.

Means to Solve the Problems

The inventors have conducted extensive investigation to solve the above-described problems, and found the following. It was found that an optical film containing a specific cellulose derivative and a specific compound can retard visible light in a wide range by substantially λ/4, and exhibits reduced variation in optical performance under variable humidity, and functions as a protective film for a polarizing plate. The cellulose derivative has a ratio $Ro_{450}/Ro_{550}$ within the specific range, $Ro_{450}$ and $Ro_{550}$ being an in-plane retardation respectively measured at wavelengths of 450 nm and 550 nm, and the glucose skeleton of the cellulose derivative contains a substituent satisfying the requirements (a) and (b) described below. The specific compound is provided with a specific orientation property when it coexists with water.

Namely, the objects of the present invention can be achieved through the following means.

1. An optical film comprising a cellulose derivative, the optical film having an in-plane retardation $Ro_{550}$ within the range of 120 to 160 nm measured at a wavelength of 550 nm under an atmosphere of a temperature of 23° C. and a relative humidity of 55%, and a ratio $Ro_{450}/Ro_{550}$ within the range of 0.65 to 0.99, $Ro_{450}/Ro_{550}$ being a ratio of an in-plane retardation $Ro_{450}$ measured at a wavelength of 450 nm to the in-plane retardation $Ro_{550}$ measured at a wavelength of 550 nm, wherein, a substituent of a glucose skeleton in the cellulose derivative satisfies the following requirements (a) and (b), and the optical film contains a compound A satisfying the following condition defined by Expression (a1).

Requirement (a): a part of the substituent contained in the glucose skeleton of the cellulose derivative is a substituent having a multiple bond, and an average degree of substitution of the substituent having a multiple bond is within the range of 0.1 to 3.0 per glucose skeleton unit.

Requirement (b): a maximum absorption wavelength of the substituent having a multiple bond is within the range of 220 to 400 nm.

$(Sw-S) \geq 0.30$  Expression (a1):

In the expression, S represents an orientation degree of the compound A in the optical film, and Sw represents an orientation degree of the compound A in the optical film in the presence of water.

2. The optical film described in the item 1, wherein the compound A satisfies the following condition defined by Expression (a2), and the compound A contains a plurality of ring structures including a heterocyclic ring in a long axis of the compound A.

$0.50 \leq (n_a - n_b) \leq 1.50$  Expression (a2):

In the expression, $n_a$ represents a refractive index in a long axis direction of the compound A, and $n_b$ represents a refractive index in an orthogonal direction to the long axis direction of the compound A.

3. The optical film described in the items 1 or 2, wherein the compound A is a compound having a structure represented by the following Formula (1).

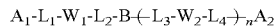  Formula (1):

In the Formula, $A_1$ and $A_2$ each represent an alkyl group, a cycloalkyl group, an aromatic hydrocarbon ring or an aromatic heterocyclic ring. $L_1$, $L_2$, $L_3$ and $L_4$ each represent a single bond or a divalent linking group. $W_1$ and $W_2$ each represent an aromatic heterocyclic ring or an aliphatic heterocyclic ring. B represents an aromatic hydrocarbon ring, an aliphatic hydrocarbon ring, an aromatic heterocyclic ring or aliphatic heterocyclic ring. n represents an integer of 0 to 5. When n is 2 or more, plural $L_3$, $L_4$ and $W_2$ may be the same or different.

4. The optical film described in any one of the items 1 to 3, wherein an average degree of substitution of the substituent having a multiple bond defined by Requirement (a) is within the range of 0.2 to 3.0 per glucose skeleton unit.

5. The optical film described in any one of the items 1 to 4, wherein the average degree of substitution of the substituent having a multiple bond at positions 2, 3, and 6 of the glucose skeleton satisfies the following Expression (1).

0<(Average degree of substitution at position 2+Average degree of substitution at position 3)−Average degree of substitution at position 6  Expression (1):

6. The optical film described in any one of the items 1 to 5, wherein the substituent having a multiple bond has a maximum absorption wavelength within the range of 220 to 300 nm.

7. The optical film described in any one of the items 1 to 6, wherein the substituent having a multiple bond contains an aromatic ring.

8. The optical film described in any one of the items 1 to 7, wherein the optical film has a thickness within the range of 20 to 60 μm.

9. The optical film described in any one of the items 1 to 8, wherein the optical film is a long film having a slow axis in a direction of 40 to 50° with respect to a longitudinal direction of the optical film.

10. A circularly polarizing plate comprising the optical film described in any one of the items 1 to 9 and a polarizer element bonded to the optical film.

11. An organic electroluminescent display device provided with the circularly polarizing plate described in item 10.

Effects of the Invention

Through the means of the present invention, provided are an optical film that can retard visible light in a wide range by substantially λ/4, exhibits a reduced variation in optical performance (tone and reflectivity) under variable humidity, and functions as a protective film for a polarizing plate; a circularly polarizing plate including the optical film; and an organic electroluminescent display device including the circularly polarizing plate as an antireflective component.

The configurations according to the present invention provide solutions to the problems described above for the following presumed reasons.

The inventors have conducted extensive investigation on the causes of the problem of unevenness in tone and reflection of displayed images that occurs depending on the use environment when a wideband λ/4 retarder is used as a circularly polarizing plate for an organic EL display device, which is produced through control of the substituents of cellulose ester so as to adjust retardation and wavelength dispersibility corresponding to phase difference.

The variation in retardation of an optical film due to absorption of moisture is probably caused by water molecules coordinated to the ester groups of the cellulose ester, and the variations in retardation is probably caused by the change of birefringence of the ester group coordinated to water. In addition, the sharp contrast and the high image quality of organic EL display devices emphasize unevenness in tone and reflection due to slight variations in retardation and wavelength dispersion that are unrecognizable in liquid crystal display devices.

The inventors have further conducted an intensive study concerning the properties of the cellulose ester resin as described above and discovered the following. An optical film containing a compound which increases an orientation degree in the presence of water will exhibit a wideband and excellent λ/4 in-plane retardation, and an organic EL display device provided with this optical film can sufficiently reduce unevenness in tone and reflection of the display device.

EMBODIMENTS TO CARRY OUT THE INVENTION

Figure 1A:
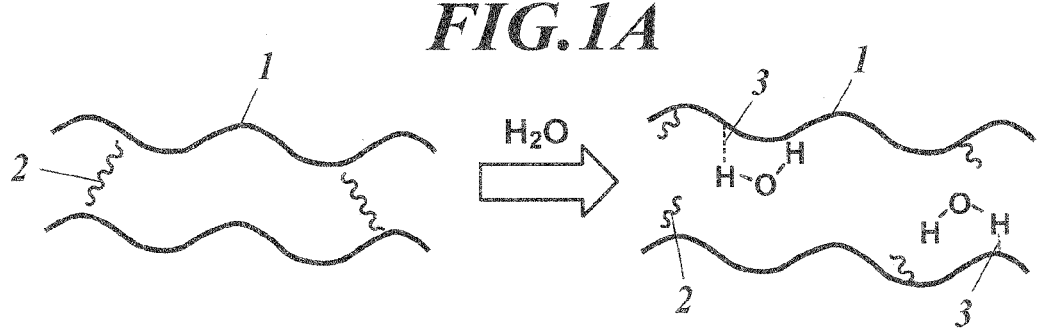
FIG. 1A is a schematic diagram A to explain an example of orientation of a compound A according to the present invention.

An optical film of the present invention has an in-plane retardation $Ro_{550}$ measured at a wavelength of 550 nm within the range of 120 to 160 nm, and a ratio of in-plane retardations $Ro_{450}/Ro_{550}$ within the range of 0.65 to 0.99, wherein the in-plane retardations $Ro_{450}$ and $Ro_{550}$ are respectively measured at wavelengths of 450 nm and 550 nm under an atmosphere of a temperature of 23° C. and a relative humidity of 55%; and substituents of glucose skeletons of the cellulose derivative are characterized in that they satisfy the above-mentioned Requirements (a) and (b); and the optical film contains a compound A satisfying the above-mentioned condition defined by Expression (a1). Such technical characteristics are common to the first to 11th aspects of the present invention.

As an embodiment of the present invention, in order to obtain the required effects of the present invention, it is preferable that the compound A satisfies the refractive index condition defined by the aforesaid expression (a2), and the compound A contains a plurality of ring structures having a heterocyclic ring in a long axis, from the viewpoint of obtaining excellent stable optical performances (for example, tone stability and reflectivity) under humidity change. That is, by the fact that the birefringence values satisfy the condition defined by expression (a2), and when a compound A according to the present invention increases an orientation degree under the presence of water, the increased amount of retardation due to the compound A can compensate the decreased amount of retardation due to cellulose in an appropriate ratio. In addition, a ling axis direction of the compound A is a direction of the longest axis of the molecule.

It is preferable that the above-mentioned compound A is a compound represented by the above-mentioned Formula (1) from the viewpoint of obtaining excellent stable optical performances (for example, tone stability and reflectivity) under humidity change.

The average degree of substitution of the substituent having a multiple bond is preferably within the range of 0.2 to 3.0 per glucose skeleton unit, in view of low variations in tone and reflectivity of an organic EL display device under external light.

The average number of substituents having a multiple bond at positions 2, 3, and 6 of the glucose skeleton preferably satisfies the aforesaid Expression (1), in view of production stability.

Satisfying the aforesaid Expression (1) promotes the wavelength dispersion control by substituents having a multiple bond; thus, a small degree of substitution of substituents having a multiple bond can achieve sufficient wavelength dispersion control. This can reduce the reaction time for introduction of substituents having a multiple bond into glucose units; thus, the elimination of other substituents can be reduced so as to enhance the production stability. Furthermore, the degree of substitution of the substituents having a multiple bond can be small, and thus the number of hydroxy groups per glucose skeleton unit can be increased. As a result, the brittleness of the film due to enhanced hydrogen bonding between resins can be reduced.

The maximum absorption wavelength of the substituents having a multiple bond is preferably within the range of 220 to 300 nm, in view of enhancement in adhesiveness and viscosity of UV-curable adhesives or UV-curable pressure-sensitive adhesives used in the production of a polarizing plate through bonding of an optical film and a polarizer element, and enhancement in transparency of visible light.

Specifically, a maximum absorption of 300 nm or less has an absorption edge outside of the visible light range and can prevent coloring of the optical film. Such a maximum absorption does not affect the adhesiveness or viscosity of the UV-curable adhesive or the UV-curable pressure-sensitive adhesive that is cured as a result of irradiation with light having a wavelength within the range of 300 to 400 nm and can enhance the adhesiveness with the polarizer element or the layer to which the polarizer element is bonded.

The term "maximum absorption wavelength" according to the present invention refers to the wavelength that achieves the largest molar adsorption coefficient within the range of 220 to 400 nm in a dichloromethane solution.

The substituent having a multiple bond preferably has an aromatic group in order to achieve high productivity.

The substituent having a multiple bond containing an aromatic structure that exhibits a large variation in birefringence depending on the wavelength can effectively control wavelength dispersion. Thus, sufficient wavelength dispersion can be achieved even with a small degree of substitution of a substituent having a multiple bond. This leads to a reduction in reaction time for introduction of the substituent having a multiple bond into glucose units, and thus, a reduction in the effect of elimination of other substituents to enhance the production stability. Furthermore, the degree of substitution of the substituent having a multiple bond can be small, and thus the number of hydroxy groups per glucose skeleton unit can be increased. As a result, the brittleness of the film due to enhanced hydrogen bonding between resins can be reduced.

Preferably, a thickness of the optical film is within the range of 20 to 60 μm, or the optical film is a long film and the slow axis is disposed within the range of 40 to 50° with respect to the longitudinal direction.

Components and embodiments of the present invention will now be described in detail. It should be noted that, throughout the specification, the term "to" indicating the numerical range is meant to be inclusive of the lower and upper limits represented by the numerals given before and after the term.

An optical film, a circularly polarizing plate, and an organic electroluminescent display device according to the present invention will now be described in detail.

<<Optical Film>>

An optical film of the present invention contains a cellulose derivative and has an in-plane retardation $Ro_{550}$ measured at a wavelength of 550 nm within the range of 120 to 160 nm, and a ratio of in-plane retardations $Ro_{450}/Ro_{550}$ within the range of 0.65 to 0.99, wherein the in-plane retardations $Ro_{450}$ and $Ro_{550}$ are respectively measured at wavelengths of 450 nm and 550 nm under an atmosphere of a temperature of 23° C. and a relative humidity of 55%; and substituents of glucose skeletons of the cellulose derivative are characterized in that they satisfy the above-mentioned Requirements (a) and (b); and the optical film contains a compound A satisfying the above-mentioned condition defined by Expression (a1). Such technical characteristics are common to the first to 11th aspects of the present invention.

Requirement (a): a part of the substituents contained in the glucose skeleton of the cellulose derivative is a substituent having a multiple bond, and an average degree of substitution of the substituents having a multiple bond is in the range of 0.1 to 3.0 per glucose skeleton unit.

Requirement (b): a maximum absorption wavelength of the substituent having the multiple bond is within a range of 220 to 400 nm.

$$(Sw-S) \geq 0.30 \qquad \text{Expression (a1):}$$

In the expression, S represents an orientation degree of the compound A in an optical film, Sw represents an orientation degree of the compound A in an optical film in the presence of water.

Preferably, the optical film is long and the slow axis is disposed within the range of 40 to 50° with respect to the longitudinal direction.

An example process of disposing the slow axis within the range of 40 to 50° with respect to the longitudinal direction is oblique stretching of a deposited unstretched film, as described below. In this embodiment, the term "optical film" refers to a film having an optical ability of retarding transmitted light by a predetermined amount; examples of such optical ability include conversion of linearly polarized light of a specific wavelength to elliptically or circularly polarized light and conversion of elliptically or circularly polarized light to linearly polarized light. In particular, the term "λ/4 retarder film" refers to an optical film having a property that shifts the in-plane phase of light having a predetermined wavelength (normally in the visible light range) by approximately ¼.

[Property of Optical Film]

An optical film according to the present invention (hereinafter also referred to as "retarder film") preferably is a wideband λ/4 retarder film that retards light within the visible range by approximately ¼ of the wavelength so as to acquire circularly polarized light.

An in-plane retardation $Ro_\lambda$ and a retardation $Rt_\lambda$ across the thickness of a retarder film according to the present invention are represented by Expressions (i) below. The character λ represents the wavelength (nm) used for the measurement of retardation. The retardation according to the present invention can be calculated after measuring the birefringence at each wavelength with, for example, Axoscan manufactured by Axometrics Inc., under an atmosphere of 23° C. and a relative humidity of 55%.

$$Ro_\lambda = (n_{x\lambda} - n_{y\lambda}) \times d$$

$$Rt_\lambda = [(n_{x\lambda} + n_{y\lambda})/2 - n_{z\lambda}] \times d \qquad \text{Expression (i):}$$

In the aforesaid expression, λ represents the wavelength (nm) used for the measurement, $n_x$, $n_y$, and $n_z$ are measured under an atmosphere of 23° C. and 55% RH, $n_x$ represents the in-plane maximum refractive index of the film. (refractive index in the direction of the slow axis), $n_y$ represents the in-plane refractive index in the direction orthogonal to the slow axis, $n_z$ represents the refractive index across the thickness orthogonal to the film plane, and d represents the thickness (nm) of the film.

Here, the retarder film according to the present invention has an in-plane retardation $Ro_{550}$ measured at a wavelength of 550 nm within the range of 120 to 160 nm, and the ratio of in-plane retardations $Ro_{450}/Ro_{550}$ is within the range of 0.65 to 0.99, where the in-plane retardations $Ro_{450}$ and $Ro_{550}$ are measured at wavelengths of 450 nm and 550 nm, respectively, where $Ro_\lambda$ represent an in-plane retardation of a wavelength λ (nm) in the retarder film.

The retardation $Ro_{550}$ according to the present invention is within the range of 120 to 160 nm, preferably 130 to 150 nm, and more preferably 135 to 145 nm. An optical film according to the present invention having an $Ro_{550}$ within the range of 120 to 160 nm achieves a retardation of approximately ¼ of the wavelength measured at a wavelength of 550 nm. A circularly polarizing plate composed of such an optical film can be installed in an organic EL display device, for example, so as to prevent reflection of indoor lighting and enhance black display characteristic in bright environments.

In the optical film of the present invention, the value of $Ro_{450}/Ro_{550}$, which is the ratio of in-plane retardations $Ro_{450}$ and $Ro_{550}$, is within the range of 0.65 to 0.99, preferably, 0.70 to 0.94, more preferably 0.75 to 0.89. If $Ro_{450}/Ro_{550}$ is within the range of 0.65 to 0.99, the retardation exhibits appropriate inverse wavelength dispersion. A long circularly polarizing plate can achieve high antireflective effects against wide-band light.

For the retardation $Rt_\lambda$ across the thickness, the retardation $Rt_{550}$ measured at a wavelength of 550 nm is preferably within the range of 60 to 200 nm, more preferably 70 to 150, most preferably 70 to 100 nm. $Rt_{550}$ within the range of 60 to 200 nm can prevent a variation in hue on a large screen at an oblique viewing angle.

[Compound A]

An aspect of the optical film of the present invention is containing a specific compound A. The specific compound A has a property of satisfying the relationship defined by the following Expression (a1) in which S represents an orientation degree of the compound A in the optical film, and Sw represents an orientation degree of the compound A in the optical film in the presence of water. That is, the compound A is provided with a property of increasing an orientation degree by 30% or more in the environment of coexisting water.

$$(Sw-S) \geq 0.30 \quad \text{Expression (a1):}$$

(Formation Mechanism of the Effect by Compound A)

At first, it will be described the technological mechanism of the compound A of the present invention which enables to increase the orientation degree in the optical film under the environment of coexisting water.

The technological feature of the present invention is related to a technology of controlling the orientation property by incorporating an organic compound as an additive having a specific structure to coexist with a water adsorbing resin which has a high affinity to water and constitutes the optical film. The present invention is based on a different technological idea from the known ideas and plural specific interactions are used together. The present invention has been achieved by founding an additive which is capable of making a certain interaction with a water adsorbing resin (cellulose resin) under the atmosphere in the existence of water.

The basic technological point of the present invention is as follows. It was discovered that a so-called "CH-π interaction", which is produced by CH portions in a main chain or a side chain of a water adsorbing resin with π electrons and which was not supposed to be a major interaction with a water adsorbing resin, is "effective interaction" which can increase an orientation degree under the atmosphere in the existence of water. In particular, by using an additive having plural portions of "CH-π interaction", it can prevent the variation of optical properties of the optical film caused by water penetrating during the storage or processing. Thus, it can prevent the variation of optical properties of the optical film by the humidity variation.

In the previously known technologies, an additive was incorporated in an optical film by co-dissolving with a water adsorbing resin by forming a hydrogen bonding with the additive through a hydrogen-bonding donating portion (e.g., a hydrogen atom in a hydroxyl group or a hydrogen atom in an amide group) existing in the water adsorbing resin or through a hydrogen-bonding accepting portion (e.g., a carbonyl oxygen atom in an ester group or a nitrogen atom contained in an aromatic heterocyclic ring).

Even when an additive does not have a hydrogen bond, there is a portion that localizes electrons in the water adsorbing resin. As a result, an additive can induce a dipole moment in a limited part or in a whole part of the resin. A "dipole-dipole interaction" can be produced by giving a suitable dipole moment to an additive. It is known a method for co-dissolving a water adsorbing resin with an additive by making use of this "dipole-dipole interaction" for the primary stabilizing mean.

On the other hand, it is hard to co-dissolve an additive having a hydrogen-bonding property in substantially non-water adsorbing resin such as polyethylene or cycloolefin polymer. In this case, it is selected and used an additive that can co-dissolve in the resin with an interaction between hydrophobic portions, which is produced by a completely different technological idea.

However, in the optical film, most of additives contained in a water adsorbing resin are compounds exhibiting specific optical functions such as UV absorption function, anti-oxidation function or birefringence property. These additives have a molecular structure containing a hydrogen-bonding donating portion or a hydrogen-bonding accepting portion. Namely, since the additive are not compounds composed of only hydrogen atoms and carbon atoms, it is easier to co-dissolve in a water adsorbing resin, and it has an advantage that compound selection can be made from a wide range.

Provided that, in the water adsorbing resin, it is supposed to use a hydrogen bond or a dipole-dipole interaction as an intermolecular force for co-dissolving of the additive as described above.

When a hydrogen bond is used as an intermolecular force for co-dissolving, the reason is as follows, a water molecule has both a hydrogen atom that is a hydrogen-bond donating portion and an oxygen atom that is a hydrogen-bond accepting portion, and the molecular size is small. The number of water molecules that penetrate during storage or processing will be extremely high compared with the number of water adsorbing resin or additives. As a result, a hydrogen-bonding portion of the water adsorbing resin becomes to bond with water molecules in a high ratio, and a hydrogen bonding property of the resin itself will be weaken. At the same time, water molecules will make hydrogen bonding to the additive, and the hydrogen bonding property will be weaken in this side. As a result, the interaction between the water adsorbing resin and the additive, that is, the orientation will be largely deteriorated by the presence of water.

When the aforesaid "dipole-dipole interaction" is used for an intermolecular force of co-dissolving, the localized ratio of electrons of the water adsorbing resin will be similarly decreased due to adsorption of water molecules (hydrogen bonding). As a result, a dipole moment will be decreased. Further, the dipole moment of the additive will be also decreased due to the same reason, and the orientation of the water adsorbing resin and the additive will be deteriorated to fail to exhibit the effect originally expected.

Based on the aforesaid assumption, the present inventors supposed that the above-described problems relating to the present invention will be solved by introducing the specific interaction to the additive which does not basically change its interaction force in the presence or absence of water molecule.

Next, it will be described interactions which can be used for an organic compound.

It is known that an aromatic compound has a ring current coming from π electrons. This will produce an induction magnetic field. When a hydrogen atom (usually, C—H) is present in the region affected by the induction magnetic field, it will receive an attraction force, and a force to come close will be acted between CH and π plan. This force is called as a "CH-π interaction".

The strength of this "CH-π interaction" is invariable even if water molecules are adsorbed to the water adsorbing resin since it is basically determined by the circulation of π electrons. The present inventors made assumption that if this "CH-π interaction" can be used for the interaction between the water adsorbing resin and the additive, the orientation variation in the presence or absence of water, which is the problem of the present invention, can be fundamentally improved.

Next, it will show an example of fixation of molecular conformation as an example of using this "CH-π interaction".

In a magenta colorant containing an image stabilizer used for a color photographic sensitive material, it is known that there is a case in which $CH_2$ protons of sulfomorpholine in an image stabilizer are largely shifted by the effect of π electrons in the phenyl group of the colorant which is in an opposing position to the image stabilizer. In the present invention, "an opposing position" indicates the state in which the CH$_2$ protons exist in a specific distance (sufficiently near distance to achieve a CH-π interaction) and near the center of the phenyl group of the colorant.

This phenomenon can be confirmed with a molecule model. The CH-π interaction between CH of the image stabilizer and the phenyl group (π) of the colorant is considered to be a driving force to form this conformation. As a proof of this idea, it was found that with a compound having a similar structure as the aforesaid colorant but when the image stabilizer does not take an opposing position to the phenyl group, the sulfomorpholine ring will not take the an opposing position to the phenyl group of the colorant as described above. Thus, in the colorant molecule which does not exhibit a CH-π interaction, the portion of the image stabilizer will be located in a far position from the colorant portion. That is, it can assume that the "CH-π interaction" according to the present invention will be an efficient intermolecular force to bind an organic compound with another organic compound.

Next, the amplitude of an effect of a ring current will be examined.

For example, when the "CH-π interaction" is formed using CH of the water adsorbing resin and π electrons of the additive, it is evident that larger π property of the additive is preferable.

As an example of representing the amplitude of this π property, it is known a NICS value (Nucleus Independent Chemical Shift).

This NICS value is an index used for quantification of aromaticity by a magnetic property. When the ring is aromatic, the center of the ring is strongly shielded by the effect of ring current, and when the ring is anti-aromatic, inversely, the center of the ring is deshieled (see, J. Am. Chem. Soc. 1966, 118, 6317). The strength of the ring current can be determined by the magnitude of NICS value. Namely, the contribution of π electrons to the aromaticity of the ring can be determined can be determined by this value.

Representative NICS values are listed in the following Table 1.

TABLE 1

| Ring | NICS value |
|---|---|
| Pyrrole ring | −14.87 |
| Thiophene ring | −14.09 |
| Furan ring | −12.42 |
| Benzene ring | −7.98 |
| Naphthalene ring | −8.11 |
| Pyrazole ring | −13.82 |
| Imidazole ring | −13.28 |
| 1H-1,2,4-triazole ring | −13.18 |
| 1,2,3-Oxadizazole ring | −12.74 |
| 1,2,5-Oxadizazole ring | −12.44 |
| 1,3-Thiazole ring | −12.82 |
| 1,2,4-Thiadiazole ring | −13.23 |

The detail of the calculation method described in Table 1 is as follows.

The NICS values described in Table 1 were calculated from the optimized structure obtained by using Gaussian 03 (Revision B.03, software made by Gaussian Inc.) with B3LYP (density functional calculation) as a calculation method, and 6-31+G as a basis function (a function which is formed from a split valence basis set added with a diffusion Gaussian function). NMR shielding constant calculation method (GIAO) was applied to obtain the values.

As described in the aforesaid Table 1, the NICS values of an aromatic heterocyclic ring (such as a pyrrole ring, a thiophene ring and a furan ring) are larger than an aromatic hydrocarbon (such as a benzene ring and a naphthalene ring). It is supposed that a compound containing a nitrogen atom, an oxygen atom, or a sulfur atom or their combination can strengthen a CH-π interaction.

It is to be noticed that orientation along the water adsorbing resin is hardly achieve by using only one intermolecular force of this kind. It is required to induce plural CH-π interactions between the additive and the water adsorbing resin. As a result of investigation by the present inventors, it was confirmed the following. When the π electrons are originated from a benzene ring, it is preferable that there exist minimum number of 3 benzene rings. Even in the case of an aromatic heterocyclic ring having a strong π property, the effect is insufficient by the existence of one aromatic heterocyclic ring. It is effective to form a structure further having another aromatic heterocyclic ring or aromatic hydrocarbon ring in the same molecule.

As describe above, the compound A according to the present invention will act to a water adsorbing resin which basically adsorb to water by employing plural CH-π interactions. This CH-π interaction is not related with water molecule or it does not lose it strength even when water molecule is adsorbed to the water adsorbing resin. This interaction has not been used before as a co-existence means of a water adsorbing resin and an additive. By this universal technology, it is hard to produce variation of an optical property of a resin composition (including a film) during storage over time, or during water processing. This technology is an invention different from the technology in a prior art literature or patent documents which accidentally describes to use a water adsorbing resin together with an aromatic compound. It is a universal and high level invention which has to be distinguished from the prior art.

Figure 1B:
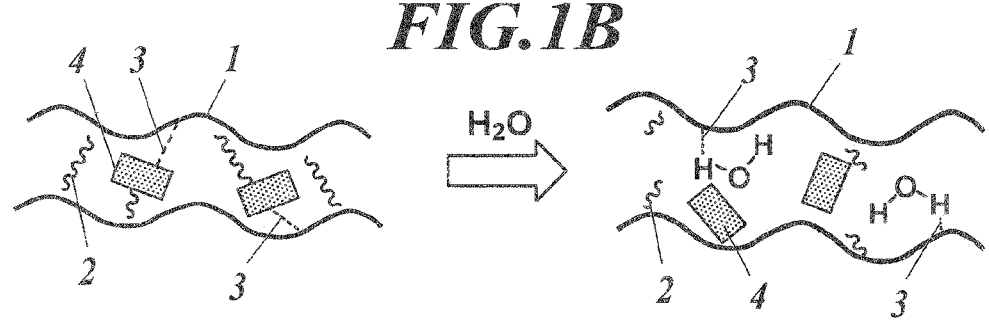
FIG. 1B is a schematic diagram B to explain an example of orientation of a compound A according to the present invention.
Figure 1C:
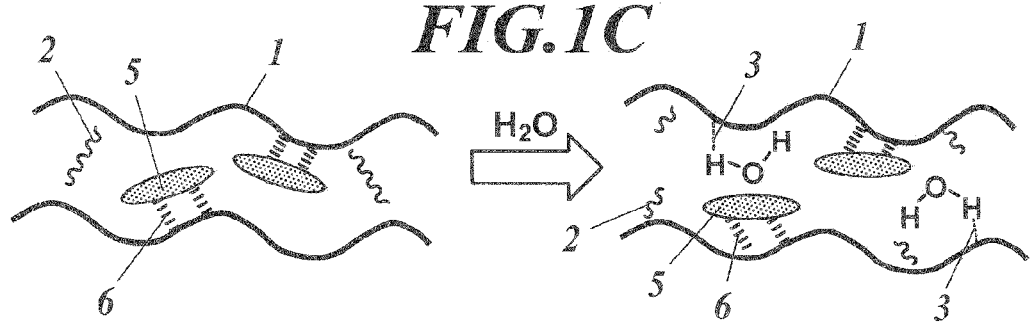
FIG. 1C is a schematic diagram C to explain an example of orientation of a compound A according to the present invention.

The content as described above will be further supplementary described by referring to FIG. 1A to FIG. 1C.

FIG. 1A to FIG. 1C each are a schematic diagram to explain an example of orientation of a compound A according to the present invention.

FIG. 1A shows an example in which an optical film changes its orientation when it adsorbs water.

In FIG. 1A, under a normal humidity atmosphere, water adsorbing resins 1 are mutually kept orientation through a dipole-dipole interaction 2. By the presence of water molecule (e.g., immersion in water), water molecules are adsorbed to the water adsorbing resins 1 through a hydrogen bonding 3. The dipole-dipole interaction 2 is broken to lose orientation.

FIG. 1B shows an example in which an optical film using an additive without CH-π interaction changes its orientation when it adsorbs water.

In FIG. 1B, under a normal humidity atmosphere, water adsorbing resins 1 are mutually kept orientation through a dipole-dipole interaction 2, and a hydrogen bonding 3 and a dipole-dipole interaction between the water adsorbing resin 1 and an additive 4. On the contrary, by the presence of water molecule (e.g., immersion in water), water molecules are adsorbed to the water adsorbing resins 1 through a hydrogen bonding 3, and the dipole-dipole interaction 2 is broken. Consequently, the additive 4 without CH-π interaction will lose interaction with the water adsorbing resin 1. Thus, orientation is lost.

FIG. 1C shows an example in which an optical film using a compound A of the present invention having a CH-π interaction is stabilized its orientation when the optical film adsorbs water.

In FIG. 10, under a normal humidity atmosphere, a dipole-dipole interaction 2 is produced between water adsorbing resins 1. Orientation is kept between the water adsorbing resin 1 and a compound A (5) through a CH-π interaction 6. Subsequently, in the presence of water molecule (e.g., immersion in water), although the dipole-dipole interaction 2 between the water adsorbing resins 1 is broken, the CH-π interaction 6 between the water adsorbing resin 1 and the compound A (5) is not affected by adsorption of water. It is not broken. Therefore, the same orientation as under a normal humidity atmosphere is kept. That is, even when the water adsorbing resin adsorbs water, orientation can be stabilized. This is a technological feature of the present invention.

(About Compound A)

In the present invention, it is characterized that the compound A according to the present invention satisfies the condition defined by the following Expression (a1).

$(Sw-S) \geq 0.30$        Expression (a1):

In the aforesaid Expression (a1), S represents an orientation degree of the compound A in the optical film, and Sw represents an orientation degree of the compound A in the optical film in the presence of water.

The orientation degrees S and Sw can be calculated from the absorbance of polarized UV absorption of the compound A contained in the film.

The absorbance used in the present invention is measured with a double beam absorption photometry. It is generally known that the error range of absorbance is minimum when absorbance A is 0.8686 based on Twyman-Lothian' law. Therefore, the absorbance value is taken at the nearest point to 0.9 for calculating the orientation degree of the present invention.

The detailed calculation method for obtaining S and Sw composing Expression (a1) is as follows.

<Calculation Method of S>

An optical film containing a compound A is sandwiched between two quartz plates, and it is left still for 24 hours at room temperature (25° C.) and relative humidity of 50%. Subsequently, polarized UV absorptions of a stretching direction and an orthogonal direction to the stretching direction each are measured. From the obtained absorption chart, it is found a wavelength X nm whose absorbance is nearest to 0.9. Then, $S_{//}$ and $S_\perp$ are read, $S_{//}$ being an absorbance at X nm in the direction in which a refractive index is largest, and $S_\perp$ being an absorbance at X nm in the orthogonal direction to the direction in which a refractive index is largest. S is calculated from the following Expression (a3).

$S=(S_{//}-S_\perp)/(S_{//}+2S_\perp)$        Expression (a3):

<Calculation Method of Sw>

An optical film containing a compound A is sandwiched between two quartz plates, and it is left still for 24 hours by immersing in a water bath at temperature of 25° C. The optical film immersed in the water bath is taken out from the water bath. Under the condition that water is kept between the two quartz plates, polarized UV absorptions of a stretching direction and an orthogonal direction to the stretching direction each are measured. From the obtained absorption chart, it is found a wavelength Y nm whose absorbance is nearest to 0.9. Then, $Sw_{//}$ and $Sw_\perp$ are read, $Sw_{//}$ being an absorbance at Y nm in the direction in which a refractive index is largest, and $Sw_\perp$ being an absorbance at Y nm in the orthogonal direction to the direction in which a refractive index is largest. Sw is calculated from the following Expression (a4).

$Sw=(Sw_{//}-Sw_\perp)/(Sw_{//}+2Sw_\perp)$        Expression (a4):

When Sw is larger than S, this means that the orientation degree of the compound A of the present invention in the optical film is increased in the presence of water. That is, the present invention is characterized in that the relationship defined by Expression (a2): (Sw−S)≥0.30 is satisfied. This means that the orientation degree of the compound A according to the present invention is increased by 30% or more in the presence of water. An object of the optical film of the present invention is to achieve an effect of preventing decrease or variation of retardation under an atmosphere of high humidity or humidity variation.

As shown in the aforesaid Expression (a1), the evaluation condition of orientation degree variation in the existence of water is more severe than the environment in which the optical film is employed. By adding a compound A provided with a property of increasing the orientation degree under the severe condition of immersed in water, it was found that it can realize an optical film that prevents variation in retardation and small color change under the employing condition of large change of humidity.

Regarding the mechanism of a change of retardation of an optical film when immersed in water, various mechanisms can be supposed. It is supposed that when a polar group (e.g., an acyl group) in a cellulose derivative is coordinated with water thorough a hydrogen bonding, birefringence of the polar group in the stretching direction is changed and retardation coming from the cellulose derivative is also changed.

The compound A according to the present invention has a feature of increasing its orientation degree in the presence of water. The birefringence in the stretching direction is also increased by the increase of orientation degree. As a result, its retardation is also increased.

It is preferable that the compound A according to the present invention satisfies the condition defined by the following Expression (a2), and contains plural ring structures including at least one heterocyclic ring in the long axis direction. That is, when the relationship of refractive index values satisfy the following Expression (a2), the increased amount of retardation derived from the compound A with increased orientation degree can suppress the decreased amount of retardation derived from the cellulose derivative in an appropriate ratio.

$0.50 \leq (n_a - n_b) \leq 1.50$        Expression (a2):

In the aforesaid Expression (a2), $n_a$ represents a refractive index in a long axis direction of the compound A, and $n_b$ represents a refractive index in an orthogonal direction to the long axis direction of the compound A. In the present invention, the long axis direction of the compound A is a direction having a longest axis in the molecule.

The aforesaid $n_a$ and $n_b$ can be calculated using Gaussian 03 (Revision B.03, software made by Gaussian Inc.).

Specific calculation can be done as follows. The value na is calculated by using the structure optimized with B3LYP/6-31G* level. The obtained polarizability tensor is diagonalized, then, the value can be calculated from the diagonalized component. Among the eigenvalues obtained after diagonalization of the polarizability tensor, the maximum component is $\alpha_a$, the second largest component is $\alpha_b$, and the minimum component is $\alpha_c$. The van der Waals volume can be also calculated starting from the structure optimized with B3LYP/6-31G* level.

From the measured polarizabilities $\alpha_a$, $\alpha_b$, and $\alpha_c$, and the van der Waals volume as described above, the refractive index can be calculated from the following Scheme 1 and Scheme 2. The allocation of the polarizabilities $\alpha_a$, $\alpha_b$, and $\alpha_c$ in the actual compound A is confirmed. When a long axis direction is not $\alpha_a$, and a short axis direction is not $\alpha_b$, the each value is replaced. The values $n_a$ and $n_b$ are calculated from these values using the following schemes.

$$n_a = \sqrt{\varepsilon_a} \qquad \text{Scheme 1}$$
$$\varepsilon_a = \frac{4\pi}{3}\frac{\alpha_a}{V}$$

$$n_b = \sqrt{\varepsilon_b} \qquad \text{Scheme 2}$$
$$\varepsilon_b = \frac{4\pi}{3}\frac{\alpha_b}{V}$$

(Effect of Compound A in the Optical Film of the Present Invention)

Figure 2:
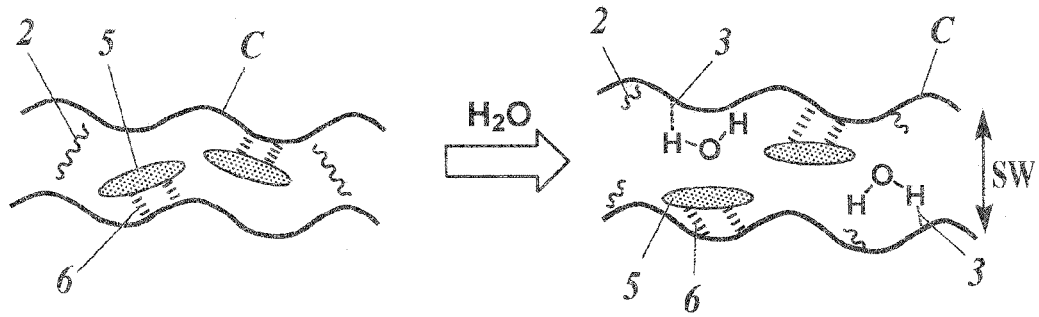
FIG. 2 is a schematic diagram to explain another example of orientation of a compound A according to the present invention.

FIG. 2 is a schematic diagram to explain an example of orientation of a compound A in an optical film of the present invention.

As shown in FIG. 2, under a normal humidity atmosphere, a cellulose derivative constituting an optical film of the present invention intrinsically has a weak interaction (a hydrogen bonding or a dipole-dipole interaction 2) between cellulose fibers C. This is one of the reasons of aggregation or tangle.

On the other hand, in the presence of water, when water penetrates near the carbonyl group of the cellulose fibers C and the cellulose fibers C is swollen (SW), the weak dipole-dipole interaction 2 between the cellulose fibers C will be broken, and the space between the cellulose fiber C chains will be increased. At this moment, the compound A(5) of the present invention which is bonded to the cellulose fiber C through the CH-π interaction 6 will take more stable structure by making use of the increased space between the cellulose chains while keeping the interaction between the cellulose fibers C, since the CH-π interaction 6 is not broken by water. Thus, the orientation degree of the compound A itself will be raised. When the compound A contains plural ring structures in the long axis direction, especially when it contains at least one heterocyclic ring with another heterocyclic ring or an aromatic ring, the CH-π interaction 6 between the ring structures and the cellulose fibers (cellulose derivative) will function at plural points. The interaction will be enforced, and it is produced a specific feature of extremely high orientation in the presence of water.

(Compound Represented by Formula (1))

In the present invention, a compound A of the present invention is preferably a compound having a structure represented by the following Formula (1).

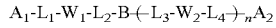

Formula (1):

In the above-described Formula (1), $A_1$ and $A_2$ each represent an alkyl group, a cycloalkyl group, an aromatic hydrocarbon ring or an aromatic heterocyclic ring. $L_1$, $L_2$, $L_3$ and $L_4$ each represent a single bond or a divalent linking group. $W_1$ and $W_2$ each represent an aromatic heterocyclic ring or an aliphatic heterocyclic ring. B represents an aromatic hydrocarbon ring, an aliphatic hydrocarbon ring, an aromatic heterocyclic ring or aliphatic heterocyclic ring. n represents an integer of 0 to 5. When n is 2 or more, plural $L_3$, $L_4$ and $W_2$ may be the same or different.

$A_1$ and $A_2$ each represent an alkyl group, a cycloalkyl group, an aromatic hydrocarbon, or an aromatic heterocyclic ring. Examples of an alkyl group represented by $A_1$ and $A_2$ are a methyl group, an ethyl group, an n-propyl group, an isopropyl group, a tert-butyl group, an n-octyl group, and a 2-ethylhexyl group. Examples of a cycloalkyl group represented by $A_1$ and $A_2$ are a cyclohexyl group, a cyclopentyl group and a 4-n-dodecylcyclohexyl group.

Examples of an aromatic hydrocarbon ring represented by $A_1$ and $A_2$ are: a benzene ring and a naphthalene ring. Examples of an aromatic heterocyclic ring represented by $A_1$ and $A_2$ are: a furan ring, a thiophene ring, a pyrrole ring, a pyrimidine ring, a pyridine ring, a pyrazine ring, a pyridazine ring, an imidazole ring, a triazole ring, an oxazole ring, a thiazole ring, and an oxadiazole ring.

An alkyl group, a cycloalkyl group, an aromatic hydrocarbon ring and an aromatic heterocyclic ring represented by $A_1$ and $A_2$ each may be substituted with any substituent.

Specific examples of the substituent are not particularly limited, and examples are as follows: a halogen atom (for example, a fluorine atom, a chlorine atom, a bromine atom, an iodine atom), an alkyl group (for example, a methyl group, an ethyl group, an n-propyl group, an isopropyl group, a tert-butyl group, an n-octyl group, a 2-ethylhexyl group), an alkenyl group (for example, a vinyl group, an allyl group), an alkynyl group (for example, an ethynyl group, a propargyl group), a cyano group, a hydroxy group, a nitro group, a carboxy group, an alkoxy group (for example, a methoxy group, an ethoxy group, an isopropoxy group, a tert-butoxy group, an n-octyloxy group, a 2-methoxyethoxy group), an acyloxy group (for example, a formyloxy group, an acetyloxy group, a pivaloyloxy group, a stearoyloxy group), an alkoxycarbonyl group (for example, a methoxycarbonyl group, an ethoxycarbonyl group), an aryloxycarbonyl group (for example, a phenoxycarbonyl group), an amino group (for example, an amino group, a methylamino group, a dimethylamino group), an acylamino group (for example, a formylamino group, an acetylamino group, a pivaloylamino group, a lauroylamino group), an alkylsulfonylamino group (for example, a methylsulfonyl amino group, a butyl sulfonyl amino group), a mercapto group, an alkylthio group (for example, a methylthio group, an ethylthio group, an n-hexadecylthio group), a sulfamoyl group (for example, an N-ethyl-sulfamoyl group, an N-(3-dodecyloxypropyl)sulfamoyl group, an N,N-dimethylsulfamoyl group, an N-acetylsulfamoyl group), a sulfo group, an acyl group (for example, an acetyl group), a carbamoyl group (for example, a carbamoyl group, an N-methylcarbamoyl group, an N,N-dimethylcarbamoyl group, an N,N-di-n-octylcarbamoyl group, an N-(methylsulfonyl)carbamoyl group), an aryl group (for example, a phenyl group, a p-tolyl group, a naphthyl group), and a heteroaryl group (for example, a 2-furyl group, a 2-thienyl group, a 2-pyridinyl group, a 2-benzothiazolyl group, a 2-pyridyl group).

$L_1$, $L_2$, $L_3$ and $L_4$ each represent a single bond or a divalent linking group. Specific examples of a linking group represented by $L_1$, $L_2$, $L_3$ and $L_4$ are selected from the group consisting of an alkylene group, an alkenylene group, an alkynylene group, —O—, —(C=O)—, —(C=O)—O—, —NR'—, —S—, —(O=S=O)—, and —(C=O)—NR'— (R' is a hydrogen atom or a substituent), or a combination thereof.

$W_1$ and $W_2$ each represent an aromatic heterocyclic ring or an aliphatic heterocyclic ring. Examples of an aromatic heterocyclic ring represented by $W_1$ and $W_2$ are: a furan ring, a thiophene ring, a pyrrole ring, a pyrimidine ring, a pyridine ring, a pyrazine ring, a pyridazine ring, an imidazole ring, a triazole ring, an oxazole ring, a thiazole ring, and oxadiazole ring. Examples of an aliphatic heterocyclic ring represented by $W_1$ and $W_2$ are: a pyrazole ring, a piperidine ring, a piperazine ring, a pyrrolidine ring, morpholine, thiomorpholine, and proline.

An aromatic heterocyclic ring or an aliphatic heterocyclic ring represented by $W_1$ and $W_2$ may be substituted with any substituent. The substituents which may be possessed by $W_1$ and $W_2$ are the same substituent groups which may be possessed by $A_1$ and $A_2$.

An aromatic heterocyclic ring is preferable as $W_1$ and $W_2$. More preferably, it is a nitrogen-containing aromatic heterocyclic ring, and still more preferably, it is a nitrogen-containing 5-membered aromatic heterocyclic ring. Most preferable rings are: an imidazole ring, a pyrazole ring, a triazole ring, and an oxadiazole ring.

B represents an aromatic hydrocarbon ring, an aliphatic hydrocarbon ring, an aromatic heterocyclic ring or an aliphatic heterocyclic ring. Examples of an aromatic hydrocarbon ring represented by B are: a benzene ring and a naphthalene ring. Examples of an aliphatic hydrocarbon ring represented by B are: a cyclohexane ring, a cyclopentane ring, a cycloheptane ring and a cyclooctane ring. Examples of an aromatic heterocyclic ring represented by B are: a furan ring, a thiophene ring, a pyrrole ring, a pyrimidine ring, a pyridine ring, a pyrazine ring, a pyridazine ring, an imidazole ring, a triazole ring, an oxazole ring, a thiazole ring, and an oxadiazole ring. Examples of an aliphatic heterocyclic ring represented by B are: a pyrazole ring, a piperidine ring, a piperazine ring, a pyrrolidine ring, morpholine, thiomorpholine, and proline.

An aromatic hydrocarbon ring, an aliphatic hydrocarbon ring, an aromatic heterocyclic ring and an aliphatic heterocyclic ring, which are represented by B, each may be substituted with any substituent. The substituents which may be possessed by B are the same substituent groups which may be possessed by $A_1$ and $A_2$.

Preferably, B is an aromatic hydrocarbon ring or an aromatic heterocyclic ring. More preferably, B is an aromatic hydrocarbon ring.

It is preferable that Formula (1) according to the present invention includes a structure having a plurality of ring structures containing a heterocyclic ring in a long axis direction.

<Exemplary Compounds Represented by Formula (1)>

In the following, exemplary compounds 1-1 to 1-30 are shown as specific examples of a compound represented by Formula (1) according to the present invention. However, a compound A which can be used in the present invention is not limited in any way by these exemplary compounds.

1-1

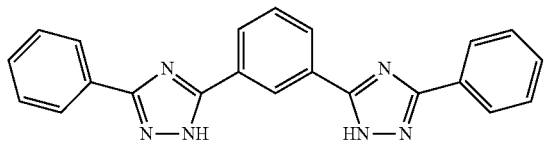

1-2

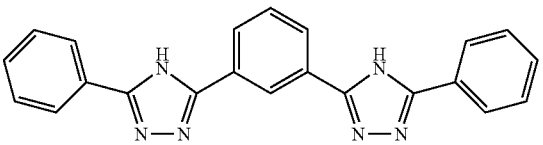

1-3

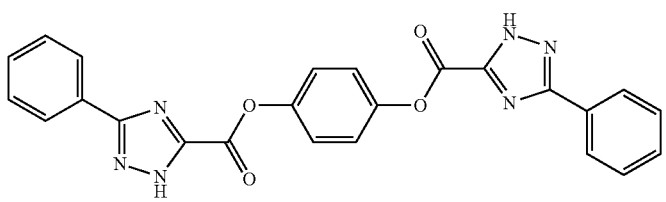

1-4

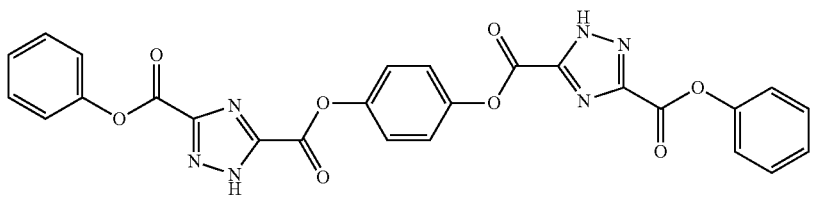

1-5

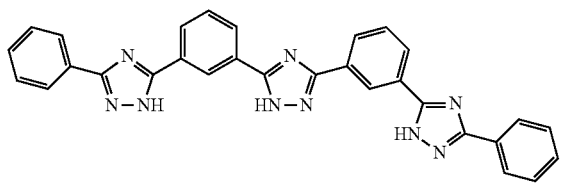

1-6

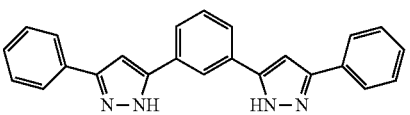

1-7

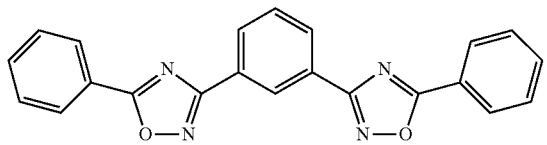

1-8

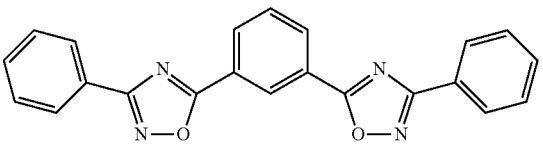

-continued
1-9
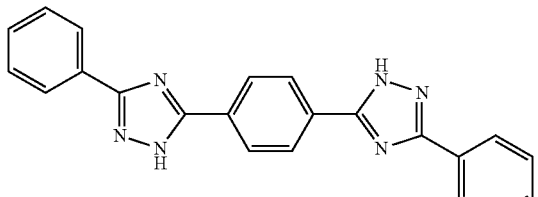
1-10
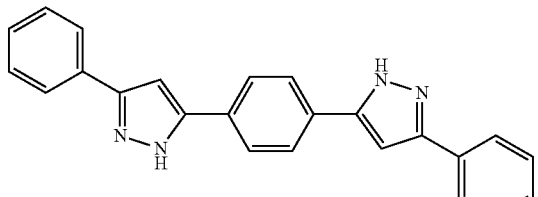
1-11
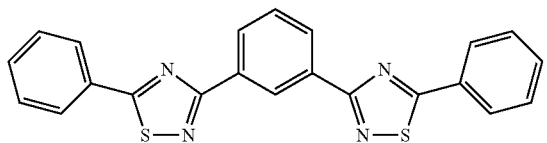
1-12
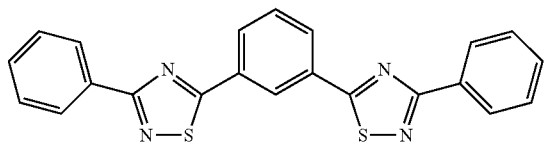
1-13
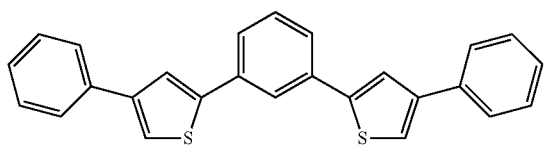
1-14
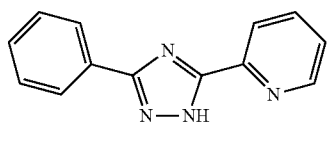
1-15
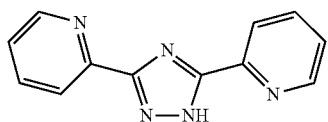
1-16
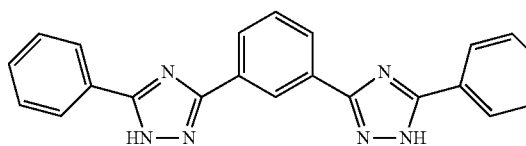
1-17
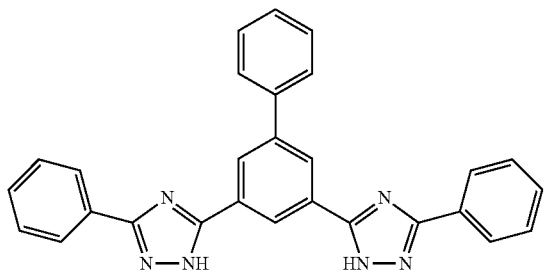
1-18
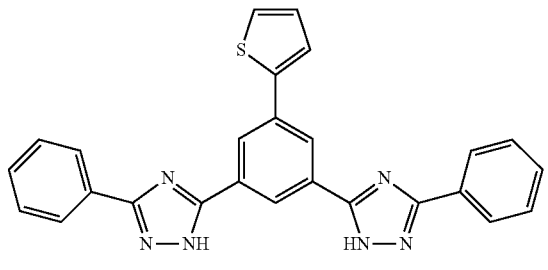
1-19
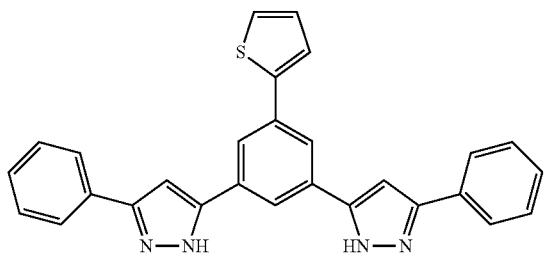
1-20
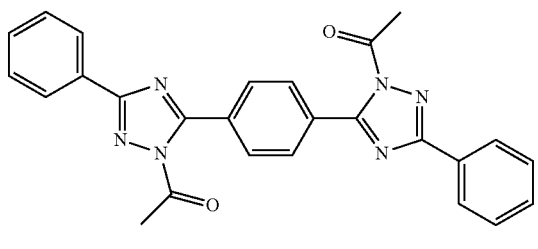
1-21
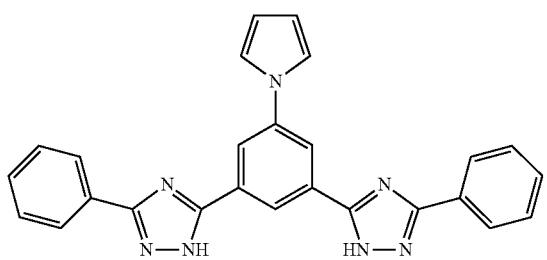
1-22
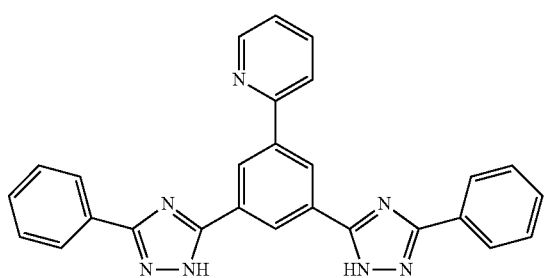

1-23
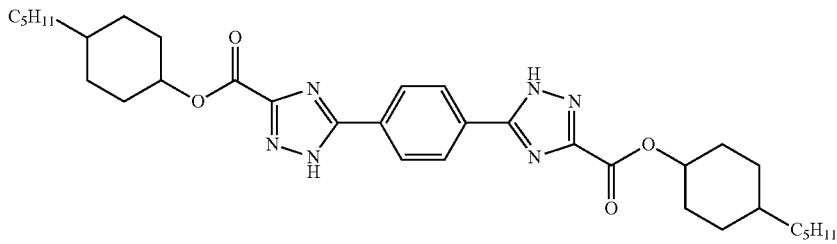
1-24
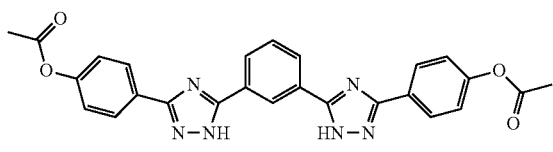
1-25
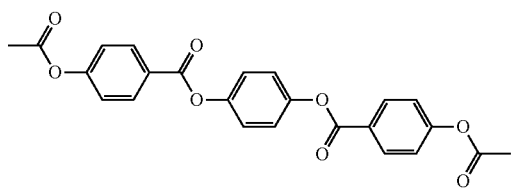
1-26
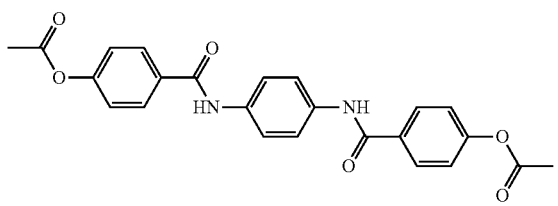
1-27
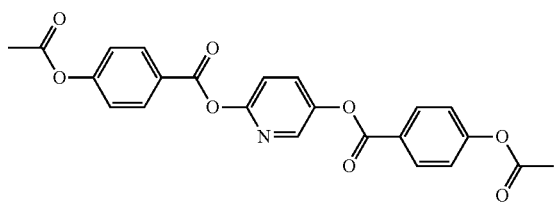
1-28
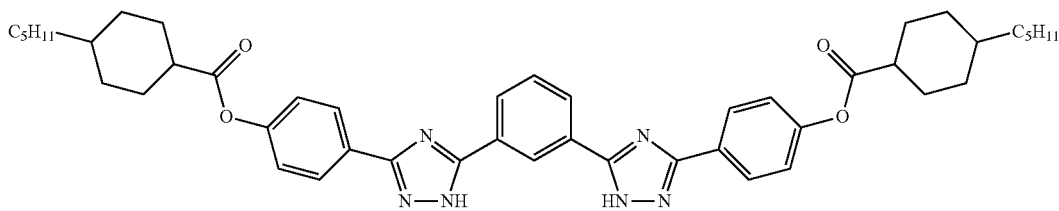
1-29
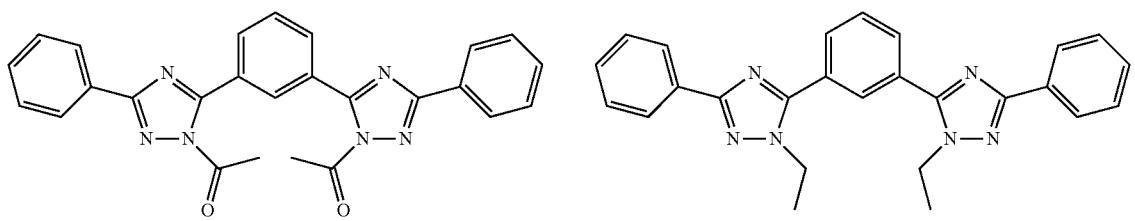
1-30
1-31
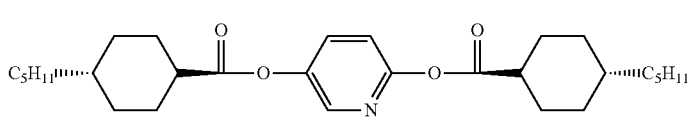
1-32
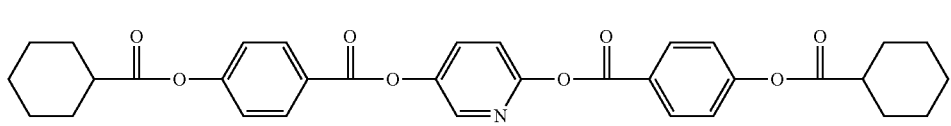

<Synthetic Example of Compound Represented by Formula (1)>

A compound represented by Formula (1) according to the present invention can be synthesized by a known method. As an example of a synthetic method, the above exemplified compound 1-1 can be synthesized according to the synthetic method shown below by referring to Tetrahedron Letters, 2005, No. 46, pp. 3429-3432.

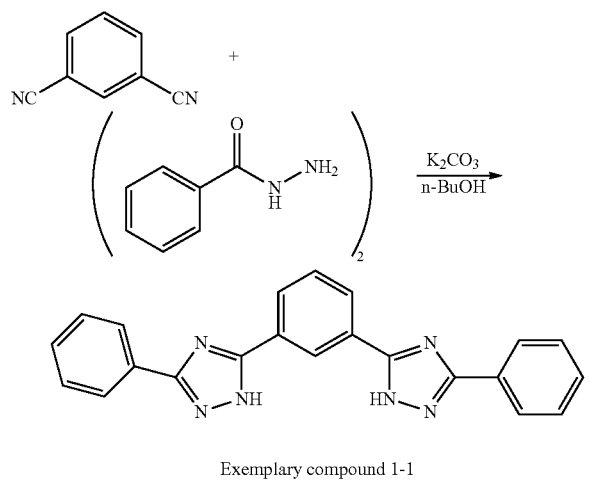

Exemplary compound 1-1

After conducting nitrogen substitution to a 1 L-four neck flask, there were added 10.0 of isophthalonitrile, 31.9 g of benzoyl hydrazine, and 150 mL of n-butanol. After stirring 30 minutes at room temperature, 18.9 g of potassium carbonate was added, and the mixture was heated for 3 hours at 130° C., and the mixture was refluxed. After cooling, the reaction solution was poured into 200 mL of water, and the solid was filtered off.

The resulting solid was dissolved in a mixture of 100 mL of 1 mol/L hydrochloric acid and 100 mL of ethyl acetate. The organic layer was washed with 50 mL of saturated brine three times. The organic layers were combined, and the solvent was distilled off by vacuum distillation to obtain 30 g of crude product. The obtained crude product was purified with silica gel chromatography (eluent hexane/ethyl acetate=1/3), and it was recrystallized from methanol. It was produced 20.7 g of exemplary compound 1-1 as white crystals (yield: 73%).

[Cellulose Derivative]

The cellulose derivative in the optical film according to the present invention has a feature of having glucose skeletons containing substituents satisfying Requirements (a) and (b) described below.

According to the First Requirement (a) of the substituents of the glucose skeletons of the cellulose derivative according to the present invention, a part of the substituent have a multiple bond, and the average degree of substitution of the substituent having a multiple bond is within the range of 0.1 to 3.0 per glucose skeleton unit. The average degree of substitution of the substituent having a multiple bond is preferably within the range of 0.2 to 1.7 per glucose skeleton unit. The average degree of substitution of the substituent having a multiple bond at positions 2, 3, and 6 of the glucose skeleton preferably satisfies the relationship: 0<(average degree of substitution at position 2+average degree of substitution at position 3)–average degree of substitution at position 6.

According to the Second Requirement (b) of the substituents of the glucose skeletons of the cellulose derivative according to the present invention, the maximum absorption wavelength of the substituent having a multiple bond is within the range of 220 to 400 nm. Furthermore, the maximum absorption wavelength of the substituent having a multiple bond is preferably within the range of 220 to 300 nm.

The cellulose derivative according to the present invention will now be described in details.

The glucose skeleton of the cellulose derivative according to the present invention is composed of glucose skeleton units represented by Formula (2) below.

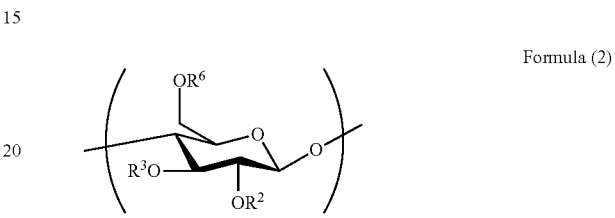

Formula (2)

In Formula (2), $R^2$ represents a substituent at position 2 of a glucose skeleton, $R^3$ represents a substituent at position 3 of a glucose skeleton, and $R^6$ presents a substituent at position 6 of a glucose skeleton. $R^2$, $R^3$, and $R^6$ may each be a hydrogen atom or any substituent that satisfies Requirements (a) and (b) described above.

(Substituent Having a Multiple Bond)

A cellulose derivative according to the present invention has a substituent having a multiple bond. The substituent having a multiple bond may be any substituent including at least one double bond or triple bond and having a maximum absorption wavelength within the range of 220 to 400 nm, and, for example, be substituents having an aromatic structure. The substituents may be aromatic groups having a combination of double and triple bonds. The aromatic groups may form bonds with electron-withdrawing or electron-releasing functional groups. Electron-releasing groups are preferably bonded to aromatic groups so as to enhance wavelength dispersion.

The cellulose derivative according to the present invention has a substituent having a multiple bond of which the average degree of substitution is within the range of 0.1 to 3.0 per glucose skeleton unit. The term "average degree of substitution" refers to the average of the total number of substituents having a multiple bond at positions 2, 3, and 6 of the glucose skeleton in the total amount of cellulose derivatives.

With reference to Formula (2), the substituents $R^2$, $R^3$, and $R^6$ having a multiple bond can be represented as —R, —OC—R, —OCNH—R, and —OC—O—R, for example, where R represents an aromatic group.

The aromatic group according to the present invention is defined as an aromatic compound in Rikagaku Jiten, (Dictionary of Physical and Chemical Science) (Iwanami Shoten, Publishers), Fourth Edition, p. 1208. The aromatic group according to the present invention may be an aromatic hydrocarbon group or an aromatic heterocyclic group, preferably an aromatic hydrocarbon group.

The aromatic hydrocarbon group preferably has a carbon atom number of 6 to 24, more preferably 6 to 12, most preferably 6 to 10. Examples of aromatic hydrocarbon groups include: a phenyl group, a naphthyl group, an anthryl group, a biphenyl group, and a terphenyl group. Preferable groups area a phenyl group, a naphthyl group, and a biphenyl group. More preferable group is a phenyl group.

An aromatic heterocyclic group preferably contains at least one of an oxygen atom, a nitrogen atom, and a sulfur atom. Examples of a heterocyclic group include: furan, pyrrole, thiophene, imidazole, pyrazole, pyridine, pyrazine, pyridazine, triazole, triazine, indole, indazole, purine, thiazoline, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzthiazole, benzotriazole, and tetrazaindene. Specific preferable aromatic heterocyclic groups are: a pyridyl group, a thiophenyl group, a triazinyl group, and a quinolyl group.

Preferable examples of an aromatic acyl group include: a benzoyl group, a phenyl benzoyl group, a 4-methylbenzoyl group, a 4-thiomethylbenzoyl group, a 4-methoxybenzoyl group, a 4-heptylbenzoyl group, a 2,4,5-trimethoxybenzoyl group, a 2,4,5-trimethylbenzoyl group, a 3,4,5-trimethoxybenzoyl group, and a naphthoyl group.

Other examples of an aromatic acyl group include: 2-thiophene carboxylic ester, 3-thiophene carboxylic ester, 4-thiazole carboxylic ester, 2-thiazole carboxylic ester, 2-furan carboxylic ester, 3-furan carboxylic ester, 4-oxazole carboxylic ester, 2-oxazole carboxylic ester, 2-pyrrole carboxylic ester, 3-pyrrole carboxylic ester, 3-imidazole carboxylic ester, 2-triazole carboxylic ester, 1-pyrrole carboxylic ester, 1-imidazole carboxylic ester, 1-pyrazole carboxylic ester, 2-pyridine carboxylic ester, 3-pyridine carboxylic ester, 4-pyridine carboxylic ester, 2-pyrazine carboxylic ester, 4-pyrimidine carboxylic ester, 2-pyrimidine carboxylic ester, 2-quinoline carboxylic ester, 2-quinoxaline carboxylic ester, 7-quinoline carboxylic ester, 9-carbazole carboxylic ester, 2-benzothiophene carboxylic ester, 2-benzofuran carboxylic ester, 2-indole carboxylic ester, 2-benzothiazole carboxylic ester, 2-benzoxazole carboxylic ester, and 2-benzoimidazole carboxylic ester.

Such aromatic groups may further include substituents that preferably do not contain a carboxy group (—C(=O)O—). A carboxy group enhances hydrophilicity and thus tends to increase the dependence of optical properties on humidity. An aromatic group has an aromatic site that is preferably unsubstituted or substituted by an alkyl or an aryl group.

(Other Substituents)

Formula (2) may have substituents other than those having a multiple bond, as long as Requirements (a) and (b) are satisfied.

Examples of such substituents, it may be cited the case where $R^2$, $R^3$, and $R^6$ each represent an aliphatic acyl group.

An aliphatic acyl group is represented by —(C=O)R, where R represents an aliphatic group. The aliphatic group site may be any one of linear, branched, and cyclic chains. The number of carbon atoms in an aliphatic acyl group is preferably within the range of 1 to 20, more preferably 1 to 12, most preferably 1 to 6.

The aliphatic group site of the aliphatic acyl group may contain one or more substituents.

The aliphatic acyl group is preferably unsubstituted and preferably any one of an acetyl group, a propionyl group, and a butyryl group.

(Synthesis of Cellulose Derivative)

The cellulose derivative according to the present invention can be produced with reference to a known method, for example, described in "Serurosu no Jiten (Dictionary of Cellulose)" (pp. 131-164) (Asakura Publishing Co. Ltd., 2000).

Specifically, unsubstituted cellulose, cellulose ester in which a part of hydroxy groups at positions 2, 3, and 6 is substituted with an ester group of an acetyl group, a propionyl group, and a butyryl group, and cellulose ether in which a part of hydroxy groups at positions 2, 3, and 6 is substituted with an ether group can be used as a raw material. Specifically, a raw material of cellulose, cellulose ester or cellulose ether is dissolved in an appropriate solvent, and it is reacted with an acid chloride or an acid anhydride in the presence of a base, such as pyridine. Thus, it can obtain a targeted cellulose derivative.

A known raw material may be used as a raw material cotton for cellulose ester or cellulose ether.

According to the present invention, the degree of substitution of the substituents in glucose skeletons can be determined by $^1$H-NMR or $^{13}$C-NMR spectroscopic procedures described in "Cellulose Communication 6, 73-79 (1999)" and "Chirality 12(9), 670-674."

Structural examples of a cellulose derivative according to the present invention and synthetic examples are shown in the following.

Table 2 shows structural examples of a cellulose derivative according to the present invention.

TABLE 2

| | Cellulose derivative | | Result | |
|---|---|---|---|---|
| No. | Cellulose raw material | Substituent | *1 | *2 |
| b1 | Cellulose acetate having a degree of substitution of acetyl group of 2.15 | 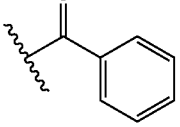 | 0.73 | 2.88 |
| b2 | Cellulose ether having a degree of substitution of methoxy group of 1.80 | | 0.93 | 2.73 |
| b3 | Cellulose ether having a degree of substitution of ethoxy group of 2.30 | | 0.55 | 2.85 |
| b4 | Cellulose acylate propionate having a degree of substitution of acetyl group of 0.19, and a degree of substitution of propionyl group of 2.56 | | 0.15 | 2.90 |
| t1 | Cellulose acetate having a degree of substitution of acetyl group of 2.15 |  | 0.22 | 2.37 |
| t2 | Cellulose ether having a degree of substitution of methoxy group of 1.80 | | 0.48 | 2.28 |
| t3 | Cellulose ether having a degree of substitution of ethoxy group of 2.30 | | 0.35 | 2.65 |
| t4 | Cellulose acylate propionate having a degree of substitution of acetyl group of 1.58, a degree of substitution of propionyl group of 0.88 | | 0.25 | 2.71 |
| p1 | Cellulose acetate having a degree of substitution of acetyl group of 2.15 |  | 0.42 | 2.57 |
| p2 | Cellulose ether having a degree of substitution of methoxy group of 1.80 | 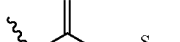 | 0.50 | 2.30 |

TABLE 2-continued

| | Cellulose derivative | | Result | |
|---|---|---|---|---|
| No. | Cellulose raw material | Substituent | *1 | *2 |
| p3 | Cellulose ether having a degree of substitution of ethoxy group of 2.30 | 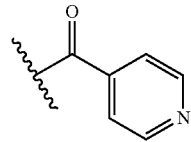 [SMILES: *C(=O)c1ccncc1] | 0.35 | 2.65 |
| p4 | Cellulose ether having a degree of substitution of ethoxy group of 2.30 | 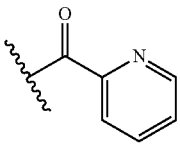 [SMILES: *C(=O)c1ccccn1] | 0.45 | 2.75 |
| m1 | Cellulose ether having a degree of substitution of methoxy group of 1.80 | 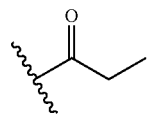 | 0.50 | 2.85 |
| | | 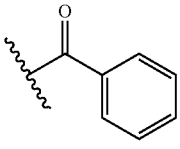 [SMILES: *C(=O)c1ccccc1] | 0.55 | |
| m2 | Cellulose ether having a degree of substitution of ethoxy group of 2.30 | 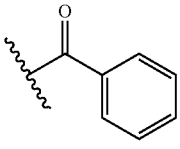 [SMILES: *C(=O)c1ccccc1] | 0.22 | 2.92 |
| | | 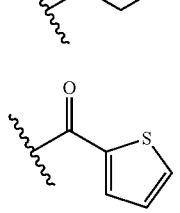 | 0.40 | |

*1: Degree of substitution
*2: Total degree of substitution

Subsequently, synthetic methods of cellulose derivatives of the present invention, which are shown in Table 2 as examples, are described.

<1: Synthesis of Cellulose Derivative b1>

A 3-L three-neck flask equipped with a mechanical stirrer, a thermometer, a condenser tube, and a dropping funnel was charged with 50 g of cellulose acetate having an acetyl substitution degree of 2.15 and 100 mL of pyridine. Then, the mixture was stirred at room temperature. To the mixture was slowly added dropwise 120 g of benzoyl chloride. The mixture was then stirred for 5 hours at 80° C. After the reaction, the mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative b1.

The average substitution degree of the substituents in glucose skeletons of cellulose derivative b1 prepared as described above was determined by $^1$H-NMR or $^{13}$C-NMR spectroscopic procedures described in "Cellulose Communication 6, 73-79 (1999)" and "Chirality 12(9), 670-674." The substitution degree of benzoate substituent having a multiple bond was 0.73, and the substitution degree of acetyl group was 2.15; which led to a total substitution degree of 2.88.

<2: Synthesis of Cellulose Derivative b2>

A 3-L three-neck flask equipped with a mechanical stirrer, a thermometer, a condenser tube, and a dropping funnel was charged with 50 g of cellulose ester having a methoxy substitution degree of 1.80 and 100 mL of pyridine. Then, the mixture was stirred at room temperature. To the mixture was slowly added dropwise 135 g of benzoyl chloride. The mixture was then stirred for 8 hours at 80° C. After the reaction, the mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative b2.

The average substitution degree of the substituents in glucose skeletons of cellulose derivative b2 prepared as described above was determined by $^1$H-NMR or $^{13}$C-NMR spectroscopic procedures. The substitution degree of benzoate substituent having a multiple bond was 0.93, and the substitution degree of methoxy group was 1.80; which led to a total substitution degree of 2.73.

<3: Synthesis of Cellulose Derivative b3>

A 3-L three-neck flask equipped with a mechanical stirrer, a thermometer, a condenser tube, and a dropping funnel was charged with 50 g of cellulose ester having an ethoxy substitution degree of 2.30 and 100 mL of pyridine. Then, the mixture was stirred at room temperature. To the mixture was slowly added dropwise 150 g of benzoyl chloride. The mixture was then stirred for 6 hours at 80° C. After the reaction, the mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative b3.

The average substitution degree of the substituents in glucose skeletons of cellulose derivative b3 prepared as described above was determined by $^1$H-NMR or $^{13}$C-NMR spectroscopic procedures. The substitution degree of benzoate substituent having multiple bonds was 0.55, and the substitution degree of ethoxy group was 2.30; which led to a total substitution degree of 2.85.

<4: Synthesis of Cellulose Derivative b4>

A 3-L three-neck flask equipped with a mechanical stirrer, a thermometer, a condenser tube, and a dropping funnel was charged with 50 g of cellulose acylate propionate having an acetyl substitution degree of 1.09 and a propionyl substitution degree of 2.56, and 100 mL of pyridine. Then, the mixture was stirred at room temperature. To the mixture was slowly added dropwise 20 g of benzoyl chloride. The mixture was then stirred for 5 hours at 80° C. After the reaction, the mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative b4.

The average substitution degree of the substituents in glucose skeletons of cellulose derivative b4 prepared as described above was determined by $^1$H-NMR or $^{13}$C-NMR spectroscopic procedures. The substitution degree of benzoate substituent having multiple bonds was 0.15, the substitution degree of acetyl group was 0.19, and the substitution degree of propionyl group was 2.56; which led to a total substitution degree of 2.90.

<5: Synthesis of Cellulose Derivative t1>

A 3-L three-neck flask equipped with a mechanical stirrer, a thermometer, a condenser tube, and a dropping funnel was charged with 50 g of cellulose acetate having an acetyl substitution degree of 2.15 and 100 mL of pyridine. Then, the mixture was stirred at room temperature. To the mixture was slowly added dropwise 30 g of thiophene-2-carbonyl chloride. The mixture was then stirred for 6 hours at 80° C. After the reaction, the mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative t1.

The average substitution degree of the substituents in glucose skeletons of cellulose derivative t1 prepared as described above was determined by $^1$H-NMR or $^{13}$C-NMR spectroscopic procedures. The substitution degree of thiophene-2-carbonyl substituent having multiple bonds was 0.22, the substitution degree of acetyl group was 2.15; which led to a total substitution degree of 2.37.

<6: Synthesis of Cellulose Derivative t2>

In a 3-L three-neck flask equipped with a mechanical stirrer was slowly added dropwise 30 g of thiophene-2-carbonyl chloride having a methoxy substitution degree of 1.80. Then, the mixture was stirred for 8 hours at 80° C. After the reaction, the mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative t2.

The average substitution degree of the substituents in glucose skeletons of cellulose derivative t2 prepared as described above was determined by $^1$H-NMR or $^{13}$C-NMR spectroscopic procedures. The substitution degree of thiophene-2-carbonyl substituent having multiple bonds was 0.48, the substitution degree of methoxy group was 1.80; which led to a total substitution degree of 2.28.

<7: Synthesis of Cellulose Derivative t3>

A 3-L three-neck flask equipped with a mechanical stirrer, a thermometer, a condenser tube, and a dropping funnel was charged with 50 g of cellulose ester having an ethoxy substitution degree of 2.30 and 100 mL of pyridine. Then, the mixture was stirred at room temperature. To the mixture was slowly added dropwise 30 g of thiophene-2-carbonyl chloride. The mixture was then stirred for 6 hours at 80° C. After the reaction, the mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative t3.

The average substitution degree of the substituents in glucose skeletons of cellulose derivative t3 prepared as described above was determined by $^1$H-NMR or $^{13}$C-NMR spectroscopic procedures. The substitution degree of thiophene-2-carbonyl substituent having multiple bonds was 0.35, the substitution degree of ethoxy group was 2.30; which led to a total substitution degree of 2.65.

<8: Synthesis of Cellulose Derivative t4>

A 3-L three-neck flask equipped with a mechanical stirrer, a thermometer, a condenser tube, and a dropping funnel was charged with 50 g of cellulose acylate propionate having an acetyl substitution degree of 1.58 and a propionyl substitution degree of 0.88, and 100 mL of pyridine. Then, the mixture was stirred at room temperature. To the mixture was slowly added dropwise 30 g of thiophene-2-carbonyl chloride. The mixture was then stirred for 5 hours at 80° C. After the reaction, the mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative t4.

The average substitution degree of the substituents in glucose skeletons of cellulose derivative t4 prepared as described above was determined by $^1$H-NMR or $^{13}$C-NMR spectroscopic procedures. The substitution degree of thiophene-2-carbonyl substituent having multiple bonds was 0.25, the substitution degree of acetyl group was 1.58, the substitution degree of propionyl group was 0.88; which led to a total substitution degree of 2.71.

<9: Synthesis of Cellulose Derivative p1>

A 3-L three-neck flask equipped with a mechanical stirrer, a thermometer, a condenser tube, and a dropping funnel was charged with 50 g of cellulose acetate having an acetyl substitution degree of 2.15 and 100 mL of pyridine. Then, the mixture was stirred at room temperature. To the mixture was slowly added dropwise 100 g of nicotinic acid chloride. The mixture was then stirred for 6 hours at 80° C. After the reaction, the mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative p1.

The average substitution degree of the substituents in glucose skeletons of cellulose derivative p1 prepared as described above was determined by $^1$H-NMR or $^{13}$C-NMR spectroscopic procedures. The substitution degree of nicotinoyl substituent having multiple bonds was 0.42, and the substitution degree of acetyl group was 2.15; which led to a total substitution degree of 2.57.

<10: Synthesis of Cellulose Derivative p2>

A 3-L three-neck flask equipped with a mechanical stirrer, a thermometer, a condenser tube, and a dropping funnel was charged with 50 g of cellulose ester having a methoxy substitution degree of 1.80 and 100 mL of pyridine. Then, the mixture was stirred at room temperature. To the mixture was slowly added dropwise 100 g of isonicotinic acid chloride. The mixture was then stirred for 6 hours at 80° C. After the reaction, the mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative p2.

The average substitution degree of the substituents in glucose skeletons of cellulose derivative p2 prepared as described above was determined by $^1$H-NMR or $^{13}$C-NMR spectroscopic procedures. The substitution degree of isonicotinoyl substituent having multiple bonds was 0.50, and the substitution degree of methoxy group was 1.80; which led to a total substitution degree of 2.30.

<11: Synthesis of Cellulose Derivative p3>

A 3-L three-neck flask equipped with a mechanical stirrer, a thermometer, a condenser tube, and a dropping funnel was charged with 50 g of cellulose ester having an ethoxy substitution degree of 2.30 and 100 mL of pyridine. Then, the mixture was stirred at room temperature. To the mixture was slowly added dropwise 100 g of isonicotinic acid chloride. The mixture was then stirred for 6 hours at 80° C. After the reaction, the mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative p3.

The average substitution degree of the substituents in glucose skeletons of cellulose derivative p3 prepared as described above was determined by $^1$H-NMR or $^{13}$C-NMR spectroscopic procedures. The substitution degree of isonicotinoyl substituent having multiple bonds was 0.35, and the substitution degree of ethoxy group was 2.30; which led to a total substitution degree of 2.65.

<12: Synthesis of Cellulose Derivative p4>

A 3-L three-neck flask equipped with a mechanical stirrer, a thermometer, a condenser tube, and a dropping funnel was charged with 50 g of cellulose ester having an ethoxy substitution degree of 2.30 and 100 mL of pyridine. Then, the mixture was stirred at room temperature. To the mixture was slowly added dropwise 100 g of picolinic acid chloride. The mixture was then stirred for 6 hours at 80° C. After the reaction, the mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative p4.

The average substitution degree of the substituents in glucose skeletons of cellulose derivative p4 prepared as described above was determined by $^1$H-NMR or $^{13}$C-NMR spectroscopic procedures. The substitution degree of pocolinoyl substituent having multiple bonds was 0.45, and the substitution degree of ethoxy group was 2.30; which led to a total substitution degree of 2.75.

<13: Synthesis of Cellulose Derivative m1>

A 3-L three-neck flask equipped with a mechanical stirrer, a thermometer, a condenser tube, and a dropping funnel was charged with 50 g of cellulose ester having a methoxy substitution degree of 1.80 and 100 mL of pyridine. Then, the mixture was stirred at room temperature. To the mixture was slowly added dropwise 100 g of propionyl chloride. The mixture was then stirred for 3 hours at 80° C. After the mixture was cooled to room temperature, 100 g of benzoyl chloride was slowly added dropwise. The mixture was then stirred for 5 hours at 80° C. The mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for six hours at 90° C., to obtain cellulose derivative m1.

The average substitution degree of the substituents in glucose skeletons of cellulose derivative m1 prepared as described above was determined by $^1$H-NMR or $^{13}$C-NMR spectroscopic procedures. The substitution degree of propionyl substituent having multiple bonds was 0.50, the substitution degree of benzoyl group was 0.55, and the substitution degree of methoxy group was 1.80; which led to a total substitution degree of 2.85.

<14: Synthesis of Cellulose Derivative m2>

A 3-L three-neck flask equipped with a mechanical stirrer, a thermometer, a condenser tube, and a dropping funnel was charged with 50 g of cellulose ester having an ethoxy substitution degree of 2.30 and 100 mL of pyridine. Then, the mixture was stirred at room temperature. To the mixture was slowly added dropwise 100 g of propionyl chloride. The mixture was then stirred for 3 hours at 80° C. After the mixture was cooled to room temperature, 100 g of thiophene-2-carbonyl chloride was slowly added dropwise. The mixture was then stirred for 5 hours at 80° C. The mixture was cooled to room temperature and then the reaction solution was added to 20 L of methanol with vigorously agitated, to precipitate a white solid. The white solid was suction filtered and rinsed three times with large volumes of methanol. The resulting white solid was dried for one day at 60° C. and then dried under vacuum for 6 hours at 90° C., to obtain cellulose derivative m2.

The average substitution degree of the substituents in glucose skeletons of cellulose derivative m2 prepared as described above was determined by $^1$H-NMR or $^{13}$C-NMR spectroscopic procedures. The substitution degree of propionyl substituent having multiple bonds was 0.22, the substitution degree of thiophene-2-carbonyl group was 0.40, and the substitution degree of ethoxy group was 2.30; which led to a total substitution degree of 2.92.

In the above-exemplified cellulose derivatives b1 to b4, t1 to t4, p1 to p4, m1 and m2, the absorption maximum wavelength of the substituent having multiple bonds in the glucose skeletons of the cellulose derivatives each was in the range of 220 to 400 nm.

<<Various Additives for Optical Film>>

The optical film of the present invention may contain various additives having various functions beside a compound A according to the present invention.

Any additive may be selected that does not impair the advantages of the present invention. Examples of such additives include retardation enhancers, wavelength-dispersion enhancers, anti-degradation agents, UV absorbers, matting agents, and plasticizers.

Representative additives that are suitable for the optical film according to the present invention will now be described.

(UV Absorber)

The optical film according to the present invention may contain a UV absorber.

Examples of a UV absorber include: oxybenzophenones, benzotriazoles, salicylate esters, benzophenones, cyanoacrylates, and nickel complexes. Preferred are benzotriazoles, which cause less coloring. Preferred UV absorbers also include the UV absorbers described in JP-A Nos. 10-182621 and 8-337574, and the polymeric UV absorbers described in JP-A No. 6-148430. If an optical film according to the present invention is used as a protective film for a polarizer, other than a retarder film, it preferably contains a UV absorber having high absorbance for ultraviolet rays with a wavelength of 370 nm or less in view of prevention of degradation of the polarizer element and the organic EL element, and low absorbance for visible light of a wavelength of 400 nm or more in view of satisfactory display of the organic EL element.

Examples of a benzotriazole UV absorber suitable in the present invention include, but should not be limited to 2-(2'-hydroxy-5'-methylphenyl)benzotriazole, 2-(2'-hydroxy-3',5'-di-t-butylphenyl)benzotriazole, 2-(2'-hydroxy-3'-t-butyl-5'-methylphenyl)benzotriazole, 2-(2'-hydroxy-3', 5'-di-t-butylphenyl)-5-chlorobenzotriazole, 2-[2'-hydroxy-3'-(3",4",5",6"-tetrahydrophthalimidemethyl)-5'-methylphenyl]benzotriazole, 2,2-methylenebis[4-(1,1,3,3-tetramethylbutyl)-6-(2H-benzotriazole-2-yl)phenol], 2-(2'-hydroxy-3'-t-butyl-5'-methylphenyl)-5-chlorobenzotriazole, 2-(2H-benzotriazole-2-yl)-6-(linear or side-chain dodecyl)-4-methylphenol, and a mixture of octyl-3-[3-t-butyl-4-hydroxy-5-(chloro-2H-benzotriazole-2-yl)phenyl]propionate and 2-ethylhexyl-3-[3-t-butyl-4-hydroxy-5-(5-chloro-2H-benzotriazole-2-yl)phenyl]propionate.

The following commercially available products can also be used as preferred UV absorbers: Tinuvin 109, Tinuvin 171, Tinuvin 326, and Tinuvin 328 (products and trademarks of BASF Japan Ltd.).

The UV absorber should be added to the cellulose derivative in an amount within the range of preferably 0.1 to 5.0 mass %, more preferably 0.5 to 5.0 mass %.

(Anti-Degradation Agent)

The optical film according to the present invention may contain anti-degradation agents as required, such as antioxidants, light stabilizers, peroxide decomposers, radical polymerization inhibitors, metal deactivators, acid scavengers, and amines. Examples of anti-degradation agents are described in JP-A Nos. 3-199201, 5-197073, 5-194789, 5-271471, and 6-107854. The content of an anti-degradation agent is preferably within the range of 0.01 to 1 mass %, more preferably 0.01 to 0.2 mass % of the cellulose solution (dope) used in the production of an optical film, in view of an effect of the anti-degradation agent and prevention of bleeding out of the anti-degradation agent to the surface of the film. Examples of a particularly preferred anti-degradation agent include butylated hydroxytoluene (abbreviation: BHT) and tribenzylamine (abbreviation: TBA).

(Matting Agent Particles)

The optical film according to the present invention preferably contains particles as a matting agent. Examples of such matting agent particles include silicon dioxide, titanium dioxide, aluminum oxide, zirconium oxide, calcium carbonate, calcium carbonate, talc, clay, fired kaolin, fired calcium silicate, hydrated calcium silicate, aluminum silicate, magnesium silicate, and calcium phosphate. Matting agent particles containing silicon are preferred for reduction in turbidity (haze); silicon dioxide is particularly preferred. The particles of silicon dioxide preferably have an average primary particle size within the range of 1 to 20 nm and an apparent specific weight of 70 g/L or more. The average primary particle size is more preferably within the range of 5 to 16 nm, in view of a reduction in haze in the optical film. The apparent specific weight is preferably within the range of 90 to 200 g/L, more preferably 100 to 200 g/L. A large apparent specific weight can provide a dispersion liquid with high concentration and thus is preferred for reducing haze and aggregation.

Normally such particles form secondary particles having an average particle size within the range of 0.05 to 2.0 μm. Such secondary particles are present in the form of aggregations of primary particles in the optical film and form irregularities within the range of 0.05 to 2.0 μm on the surface of the optical film. The average secondary particle size is preferably within the range of 0.05 to 1.0 μm, more preferably 0.1 to 0.7 μm, most preferably 0.1 to 0.4 μm. The size of the primary and secondary particles is determined by the diameter of a circumscribed circle of a particle in the optical film observed with a scanning electron microscope. The average particle size is determined through observation of 200 particles at different locations and calculation of the average particle size.

Examples of a commercially available product of silicon oxide particles include Aerosil R972, R972V, R974, R812, 200, 200V, 300, R202, OX50, and TT600 (products and trademarks of Nippon Aerosil Co., Ltd.). Examples of commercially available products of zirconium oxide particles include Aerosil R976 and R811 (products and trademarks of Nippon Aerosil Co., Ltd.).

Aerosil 200V and Aerosil R972V contain silicon dioxide particles having an average primary particle size of 20 nm or less and an apparent specific weight of 70 g/L Or more, and are particularly preferred for maintenance of low haze in the optical film and reduction of the friction coefficient of the optical film.

The matting agent particles are preferably prepared through the procedure described below and compounded to the optical film. That is, a solvent and matting agent particles are mixed by agitation to prepare a dispersion of matting agent particles in advance; this dispersion of matting agent particles is dissolved in various additive solutions, which are prepared separately and have a cellulose derivative concentration of less than 5 mass %; and each of the additive solutions is mixed with a main cellulose derivative dope.

The hydrophobic surfaces of the matting agent particles facilitate trap of hydrophobic additives on the surfaces of the matting agent particles. These trapped additives serve as cores and promote aggregation of the additives. Thus, preliminary preparation of a mixture of a relatively hydrophilic additive and a dispersion of matting agent particles and addition of a hydrophobic additive to this mixture can reduce aggregation of the additive particles on the surface of the matting agent particles. This preferably reduces haze in the optical film and light leakage in a black display mode of the organic EL display device including the optical film.

The dispersion of matting agent particles, the additive solution, and the cellulose derivative dope are preferably mixed with an inline mixer. Any mixing process may be used in the present invention. The silicon dioxide content in a solution of silicon dioxide particles dispersed in a solvent is preferably in the range of 5 to 30 mass %, more preferably 10 to 25 mass %, and most preferably 15 to 20 mass %. At a certain content of silicon dioxide in a solution, higher dispersion is preferred because of lower turbidity and reduction in haze and aggregation. The final content of the matting agent in the cellulose derivative dope is preferably within the range of 0.001 to 1.0 mass %, more preferably 0.005 to 0.5 mass %, and most preferably 0.01 to 0.1 mass %.

[Production of Optical Film Containing Cellulose Derivative]

The optical film according to the present invention can be produced through any process without specific limitation. A preferred process is a solvent casting method (solution deposition method). In solvent casting, an optical film is produced from a solution of a cellulose derivative dissolved in an organic solvent (hereinafter the solution is also referred to as "dope").

(Solution Casting)

A preferred embodiment of the optical film according to the present invention can be produced through solution casting as described above. Solution casting includes the following steps.

(1) A step of preparing a dope through dissolution of a cellulose derivative satisfying the properties defined in the present invention and various additives in an organic solvent by heat;
(2) A step of casting the prepared dope onto a belt or drum-shaped metal support;
(3) A step of drying the cast dope into a web;
(4) A step of separating the web from the metal support; stretching or contracting the separated web;
(5) A step drying the stretched or contracted web; with including a step of reeling the finished film.

The dope is cast onto a drum or band, and the solvent is evaporated to form a film. The concentration of the precast dope is preferably adjusted to have a solid content within the range of 18 to 35 weight %. The surface of the drum or band is preferably mirror-finished. The dope is preferably cast onto a drum or band having a surface temperature of 10° C. or lower. By using the prepared cellulose derivative solution (dope), it can be cast to form a film of two or more layers.

The drying process in solvent casting is described in U.S. Pat. Nos. 2,336,310, 2,367,603, 2,492,078, 2,492,977, 2,492,978, 2,607,704, 2,739,069, and 2,739,070, UK Patent Nos. 640731 and 736892, Japanese Examined Patent Application Publication Nos. 45-4554 and 49-5614, and JP-A Nos. 60-176834, 60-203430, and 62-115035. These can be referred to. The cast film can be dried on the drum or band through blasting of air or inert gas, e.g., nitrogen.

(Stretching Step)

The optical film (retarder film) according to the present invention is characterized in that the in-plane retardation $Ro_{550}$ measured at a wavelength of 550 nm is within the range of 120 to 160 nm, as described above, and a required in-plane retardation $Ro_{550}$ can be achieved through stretching of an optical film prepared as described above.

Any stretching process may be used in the present invention. Examples of a stretching process include longitudinal stretching of a film between multiple rollers turning at different rates, longitudinal stretching of a web of which the edges are fixed with clips or pins and the distances between the clips or pins is extended in the conveying direction, and transverse stretching through extension of the distance between the clips or pins in the lateral direction. These processes may be used alone or in combination.

In the present invention, as a stretching method, the film may be stretched horizontal or vertical to the direction of film formation or may be stretched in both directions. The bidirectional stretching may be performed simultaneously or separately. Stretching with a tenter is preferred because linearly driven clips can achieve smooth stretching with reduced risk of breaking.

In a stretching process, the film is usually stretched in the transverse direction (TD) and contracted in the machine direction (MD). Oblique conveyance of the film during contraction enhances the retardation because the directions of the main chains can be readily aligned. The contraction rate can be determined by the angle of conveyance.

Figure 3:
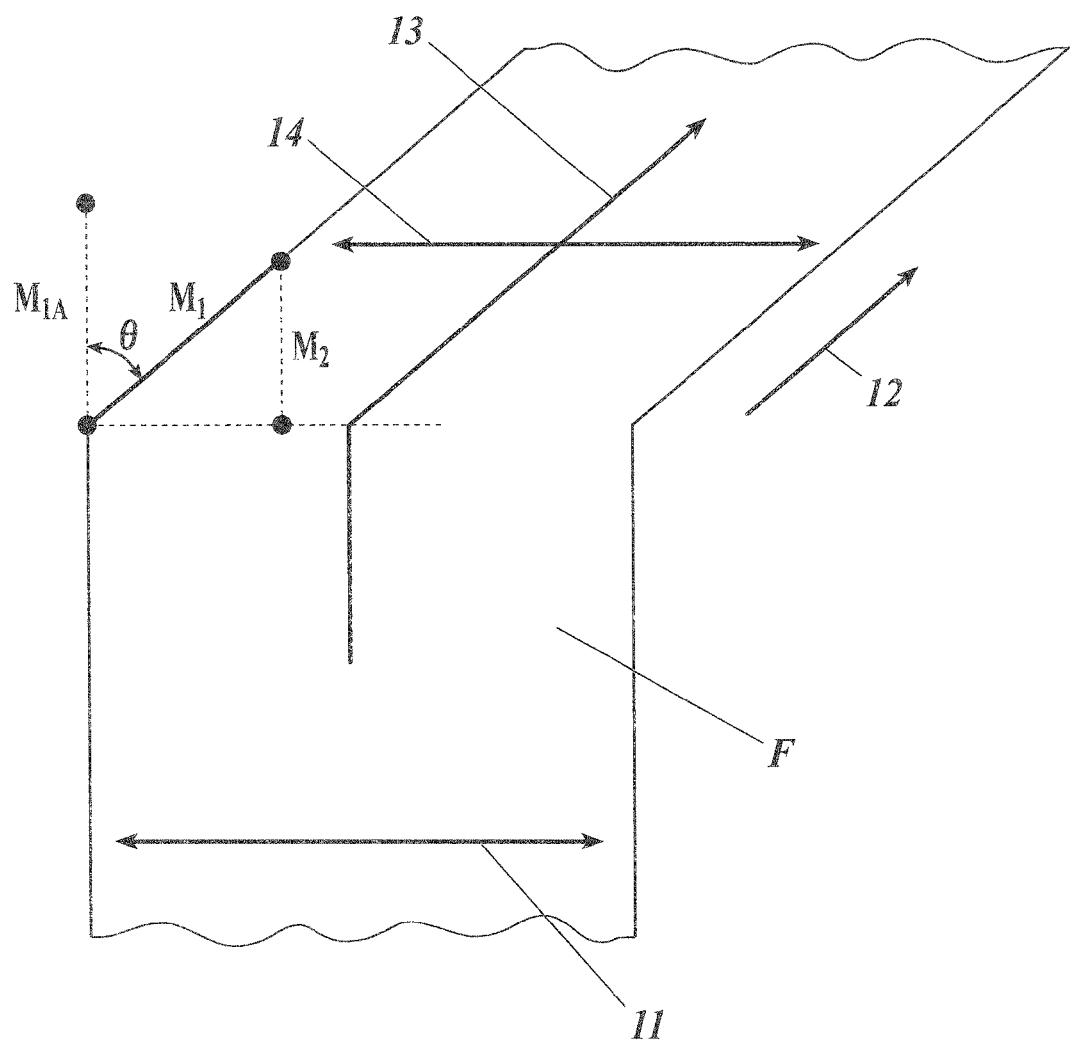
FIG. 3 is a schematic view illustrating a contraction rate in oblique stretching.

FIG. 3 is a schematic view illustrating the contraction rate in oblique stretching.

With reference to FIG. 3, an optical film F obliquely stretched in a direction denoted by reference numeral 12 is contracted to a length $M_2$ through oblique bending. That is, if the grippers clamping the optical film F continue to move forward without turning at an angle θ, the grippers should move forward by a distance $M_{1A}$ in a predetermined time. Actually, the grippers turn at an angle θ and move forward by a distance $M_1$ (where $M_1=M_{1A}$). At this time, the grippers move by a distance $M_2$ in the film entering direction (the direction orthogonal to the transverse direction (TD) 11), and thus, the optical film F is contracted by a length $M_3$ (where $M_3=M_1-M_2$).

The contraction rate (%) is defined as:

$$\text{Contraction Rate (\%)}=(M_1-M_2)/M_1\times 100$$

$$M_2=M_1\times\sin(90-\theta),$$

where θ represents the bending angle. Thus, the contraction rate is defined as:

$$\text{Contraction Rate (\%)}=(1-\sin(90-\theta))\times 100$$

With reference to FIG. 3, the transverse direction (TD) is denoted by reference numeral 11, the machine direction (MD) is denoted by reference numeral 13, and the slow axis is denoted by reference numeral 14.

In consideration of productivity of a long circularly polarizing plate, the optical film (retarder film) according to the present invention preferably has an orientation angle of 45°±2° from the conveying direction to achieve roll-to-roll bonding with the polarizing film.

(Stretching by Oblique Stretching Machine)

A procedure of oblique stretching in a 45° angle will now be described. An oblique stretching machine is preferably used in a method of producing an optical film according to the present invention to provide an oblique orientation to the stretched optical film.

An oblique stretching machine suitable for the present invention is preferably a film stretching machine that can vary rail patterns to establish any desired orientation angle in a film and align with high precision the orientation axis of the film across the transverse direction of the film equally to the right and left, and control the thickness and the retardation of the film with high precision.

Figure 4:
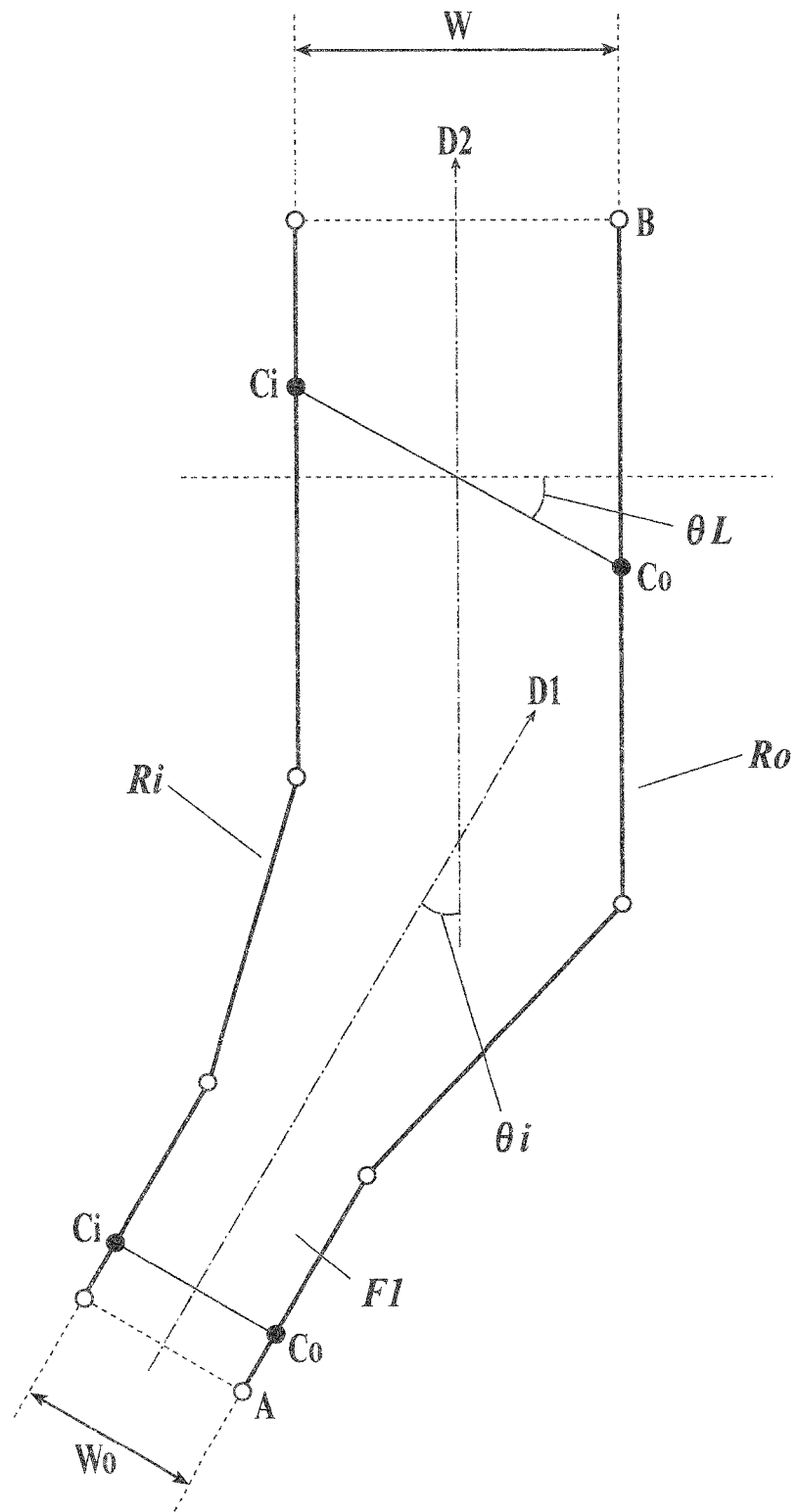
FIG. 4 is a schematic view illustrating an example of a rail pattern of an oblique stretching machine that is applicable to a method of producing a λ/4 retarder film according to the present invention.

FIG. 4 illustrates an example rail pattern of an oblique stretching machine that is suitable for the production of an optical film according to the present invention. FIG. 4 illustrates a mere example, and any other oblique stretching machine may also be used in the present invention.

In an oblique stretching machine illustrated in FIG. 4, the feeding direction D1 of a long film roll F1 usually intersects the reeling direction D2 of the stretched film F2 at a feeding angle θi. The feeding angle θi may be any angle more than 0° and less than 90°. In the present invention, the term "long" refers to a length that is at least five times the film width, preferably 10 times or more.

The edges of the long film roll F1 are supported by left and right grippers Ci and Co (tenters) at the inlet of the oblique stretching machine (position A in the drawing). As the grippers Ci and Co move, the film roll F1 also moves. The left and right grippers Ci and Co, which face each other in a direction substantially orthogonal to the forward direction (feeding direction D1) of the film at the inlet of the oblique stretching machine (position A in the drawing), move along asymmetric rails Ri and Ro, and release the film held by the tenters at the position where stretching is completed (position B in the drawing).

The left and right grippers which face each other at the inlet of the oblique stretching machine (position A in the drawing) move on the asymmetric rails Ri and Ro, and eventually the gripper Ci moving on the Ri moves ahead of the gripper Co moving on the Ro.

That is, the grippers Ci and Co, which are facing each other in a direction substantially orthogonal to the feeding direction D1 of the film at the inlet A of the oblique stretching machine (where the grippers first clamps the film), change their relative positions such that the straight line between the grippers Ci and Co tilt by an angle θL from the direction substantially orthogonal to the reeling direction D2 of the film at position B where the stretching of the film is completed.

The film roll F1 is obliquely stretched through the procedure described above. The term "substantially orthogonal" refers to an angle of 90±1°.

More specifically, a method of producing an optical film according to the present invention should include a step of oblique stretching using tenters that can perform oblique stretching as described above.

The stretching machine heats a film roll to a predetermined stretching temperature and obliquely stretches the film. The stretching machine includes a heating zone, left and right rails on which grippers move to convey the film, and multiple grippers that move on the rails. Both edges of the film fed into the inlet of the stretching machine are clamped by the grippers; the film is guided through the heating zone; and the film is released from the grippers at the outlet of the stretching machine. The film released from the grippers is wound around a core. The rails follow endless and continuous paths. Thus the grippers that have released the film at the outlet of the stretching machine move along the exterior and continuously returns to the inlet.

The rail pattern of the stretching machine is asymmetric. The rail pattern can be manually or automatically controlled depending on the orientation angle and stretching rate of the long stretchable film to be produced. The oblique stretching machine according to the present invention preferably includes rails and freely adjustable rail joins, which can be arranged in a desired rail pattern (marks "o" in FIG. 4 indicate example joints).

The grippers of the stretching machine in the present invention move at a constant rate while maintaining regular intervals with the preceding and succeeding grippers. The moving rate of the grippers can be appropriately selected. A typical rate is 1 to 100 m/min. The difference in moving rates of the left and right grippers is typically 1% or less of the moving rates, preferably 0.5% or less, more preferably 0.1% or less. That is, a difference in the moving rates of the left and right edges of the film at the stretching outlet readily causes wrinkles or biases in the film at the stretching outlet. Thus, the moving rates of the left and right grippers should be substantially identical. In a typical stretching machine, the moving rate fluctuates on an order of seconds or less due to factors such as the pitch of the teeth on a sprocket driving the chain and the frequency of the driving motor. Such fluctuation often reaches several percent of the moving rates but does not apply to the difference in moving rates concerned in the present invention.

The rails of the stretching machine suitable for the present invention control the trajectories of the grippers and often bend at an acute angle particularly in regions where the film is conveyed obliquely. The grippers should move along a curve in such regions so as to avoid interference of grippers due to an acute bending angle or local concentration of stress.

According to the present invention, both edges of the long-film roll F1 are clamped by a sequence of left and right grippers at the inlet of the oblique stretching machine (position A in FIG. 4) and are moved forward as the grippers move. The left and right grippers facing each other in a direction substantially orthogonal to the forward direction (feeding direction D1) of the film at the inlet of the stretching machine (position A in FIG. 4) move through the heating zone including a preheating subzone, a stretching subzone, and a thermal fixing subzone on the asymmetric rails.

In the preheating subzone, the grippers clamping both edges of the film at the inlet of the heating zone move forward while maintaining regular intervals.

In the stretching subzone, the intervals of the grippers clamping both edges of the film increase to a predetermined length. In the stretching subzone, the film is obliquely stretched as described above. If required, the film may be stretched vertically or horizontally before the oblique stretching. In oblique stretching, as the film turns, it contracts in the direction in the MD direction (the fast axis direction), which is a direction orthogonal to the slow axis.

Contraction of the optical film according to the present invention in a direction orthogonal to the stretching direction (fast axis direction) after stretching rotates, for example, the orientation of optical controllers (e.g., retardation enhancers and wavelength-dispersion enhancers), which is misaligned from the main chains of the cellulose derivative, which is matrix resin, so as to align the main axes of the optical controllers with the main chains of the cellulose derivative. As a result, the refractive index $n_{y280}$ along the fast axis at 280 nm in the ultraviolet range can significantly increase and the tilt of the $n_y$ normal wavelength dispersion in the visible light range becomes steep.

In the thermal fixing subzone, the distance of the grippers clamping both edges of the film is fixed downstream of the stretching subzone, and the grippers move in parallel with each other. After passing through the thermal fixing subzone, the film may pass through an additional subzone (cooling subzone) having a temperature lower than or equal to the glass transition temperature Tg of the thermoplastic resin of the film. The rails may be arranged in a pattern that reduces the distance between opposing grippers, in consideration of the contraction caused by cooling of the film.

The temperatures of the subzones are preferably set within the following ranges, where Tg is the glass transition temperature of the thermoplastic resin: (Tg) to (Tg+30° C.) in the preheating subzone; (Tg) to (Tg+30° C.) in the stretching subzone; and (Tg−30° C.) to (Tg) in the cooling subzone.

The temperature in the stretching subzone may vary so as to reduce unevenness in the thickness of the film across the width direction. The temperature in the width direction can be varied in the stretching subzone through known processes, such as varying the degree of opening of the nozzles feeding hot air into a temperature-controlled chamber along the width direction or varying the heat from heaters aligned in the width direction.

The lengths can be appropriately selected for the preheating subzone, the stretching subzone, the contraction subzone, and the cooling subzone. The length of the preheating subzone is typically within the range of 100 to 150% of that of the stretching subzone, and the length of the thermal fixing subzone is typically within the range of 50 to 100% of that of the stretching subzone.

The stretching rate (W/Wo) in the stretching process is preferably within the range of 1.3 to 3.0, more preferably 1.5 to 2.8. A stretching rate within such a range can reduce the unevenness in the thickness across the width. Varying the stretching temperature along the width direction in the stretching subzone of the oblique stretching machine can reduce the unevenness in the thickness along the width direction. Wo represents the width of the film before stretching, and W represents the width of the film after stretching.

Examples of oblique stretching processes suitable for the present invention include, in addition to that illustrated in FIG. 4, those illustrated in FIGS. 5A to 5C and FIGS. 6A and 6B.

Figure 5A:
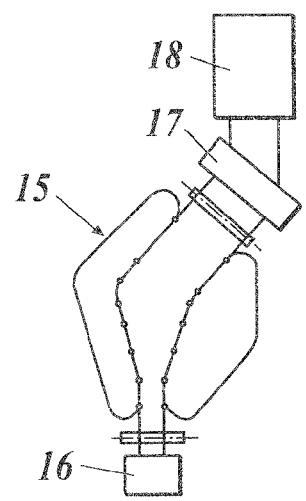
FIG. 5A is a schematic view illustrating an example of a method of producing a λ/4 retarder film (an example method of feeding a long-film from a roll and obliquely stretching the film) according to an embodiment of the present invention.
Figure 5B:
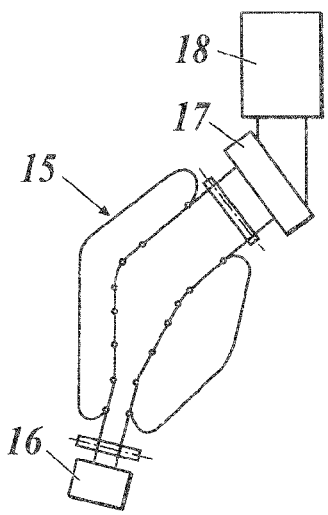
FIG. 5B is a schematic view illustrating an example of a method of producing a λ/4 retarder film (an example method of feeding a long-film from a roll and obliquely stretching the film) according to an embodiment of the present invention.
Figure 5C:
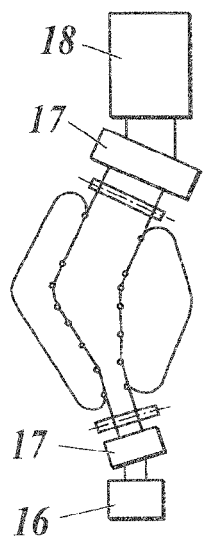
FIG. 5C is a schematic view illustrating an example of a method of producing a λ/4 retarder film (an example method of feeding a long-film from a roll and obliquely stretching the film) according to an embodiment of the present invention.
Figure 6A:
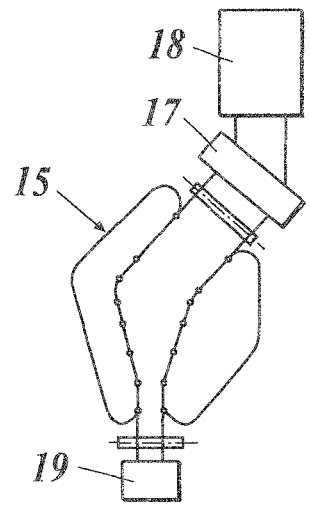
FIG. 6A is a schematic view illustrating an example of a method of producing a λ/4 retarder film (an example method of continuously and obliquely stretching a long film without reeling the film) according to an embodiment of the present invention.
Figure 6B:
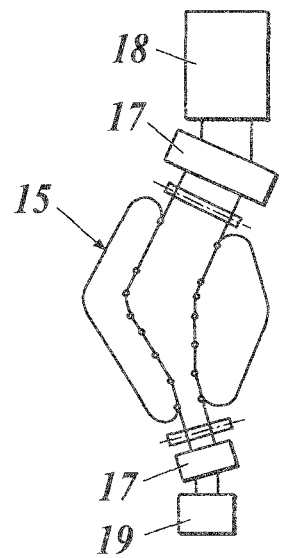
FIG. 6B is a schematic view illustrating another example of a method of producing a λ/4 retarder film (an example method of continuously and obliquely stretching a long film without reeling the film) according to an embodiment of the present invention.

FIGS. 5A to 5C illustrate example methods of producing an optical film (example methods of feeding a film from a long-film roll and obliquely stretching the film) according to the present invention, and illustrate arrangement patterns for reeling the film into a long-film roll and then feeding the film for oblique stretching. FIGS. 6A and 6B illustrate example methods of producing an optical film (example methods of obliquely stretching a film without reeling the film from a roll) according to the present invention, and illustrate arrangement patterns for continuously stretching the film obliquely without reeling the film from the roll.

In FIGS. 5A to 5C and FIGS. 6A and 6B, reference numeral 15 represents an oblique stretching machine, reference numeral 16 represents a film feeder, reference numeral 17 represents a conveying-direction changer, reference numeral 18 represents a winder, and reference numeral 19 represents a film former.

The film feeder 16 is preferably slidable and pivotable at a predetermined angle to the inlet of the oblique stretching machine 15 to feed a film to the inlet of the oblique stretching machine 15 or is preferably slidable and feeds a film to the inlet of the oblique stretching machine 15 through the conveying-direction changer 17. FIGS. 5A to 5C illustrate different arrangement patterns with the film feeder 16 and the conveying-direction changer 17 disposed at different positions. FIGS. 6A and 6B illustrate arrangement patterns for direct feeding of the film deposited by the film former 19 to the stretching machine 15. The film feeder 16 and the conveying-direction changer 17 positioned in this way reduces the width of the entire apparatus and enables precise control of the feeding position and angle of the film. This can provide a long stretched film having low variations in thickness and optical parameters. The film feeder 16 and conveying-direction changer 17 effectively prevent insufficient gripping of the film by the left and right clips.

The winder 18 is disposed at a predetermined angle to the outlet of the oblique stretching machine 15 for reeling of the film. In this way, the reeling position and angle of the film can be precisely controlled so as to acquire a long stretched film having low variations in the thickness and optical parameters. Thus, wrinkles in the film can be surely prevented, and the reeling efficiency of the film can be enhanced. Thus, a long film can be reeled. According to the present invention, the reeling tension T (N/m) of the stretched film is controlled within the range of 100 N/m<T<300 N/m, preferably 150 N/m<T<250 N/m.

(Melt Film Formation Method)

The optical film (retarder film) according to the present invention can be prepared through melt film formation method, other than solution casting method described above. In the melt film formation method, a composition containing a cellulose derivative and additives, such as a plasticizer, is heated to a predetermined temperature at which the composition melts into a fluid. The melt containing fluid thermoplastic resin is cast to form a film.

Melt film formation method can be categorized into different methods of, for example, melt extrusion molding, press molding, inflation molding, injection molding, blow molding, and stretch molding. Among these methods, melt extrusion molding is preferred in view of superior mechanical strength and surface precision.

Normally, it is preferred to perform preliminary kneading and pelletization of several raw materials used in extrusion molding. Pellets can be prepared through known procedures. For example, a dry cellulose derivative, a plasticizer, and other additives can be fed to an extruder through a feeder, kneaded in a single or double shaft extruder, extruded in the form of strands from a die, cooled by water or air, and cut into pellets.

The additives may be mixed before feeding to the extruder or supplied through individual feeders. Preliminary mixing is preferred for small amounts of additives, such as particles of matting agents and antioxidants, to yield a homogeneous mixture.

The extruder used for pelletization should process the material at a low temperature to reduce shear force and degradation (reduction in molecular weight, colorization, and gel formation) in the resin. For example, a preferred double-shaft extruder has deep-groove screws that rotate in the same direction. Engaged screws are preferred for uniform kneading.

The resulting pellets are used to form a film. Alternatively, non-pelletized, powdered raw materials can be supplied to the extruder through a feeder, heated and melted, and used to form a film.

The pellets in a single or double shaft extruder are melted at a temperature within the range of 200 to 300° C. and extruded, fed through a leaf disc filter for removal of foreign material, and cast from a T die into a film. The resulting film is nipped between a cooling roller and an elastic touch roller to solidify the film on the cooling roller.

The pellets should be fed from a feed hopper to the extruder under a vacuum, reduced pressure, or inert gas atmosphere for prevention of oxidative decomposition.

The extrusion rate should be stabilized through the use of a gear pump, for example. The filter used to remove foreign materials is preferably a sintered stainless steel fiber filter. The sintered stainless steel fiber filter is prepared through compression and sintering of intertwined stainless steel fibers into a single product. The thickness of the fiber and the degree of compression are varied to vary the density, thereby controlling the degree of filtration.

Additives such as plasticizers and particles may be preliminarily mixed with the resin or may be mixed with the resin in the extruder. A static mixer, for example, should be used for uniform mixing.

The temperature of the surface of the film adjacent to the elastic touch roller that is nipped between the cooling roller and the elastic touch roller is preferably within the range of Tg to Tg 110° C. Any known elastic touch roller having an elastic surface may be used for this purpose. A commercially available elastic touch roller, which is also referred to as a clamping rotator, may also be used.

When separating the film from the cooling roller, the tension is preferably controlled so as to prevent deformation of the film.

The resulting film can be stretched and contracted through a stretching operation performed after passing through the cooling roller. A known roller stretching machine or an oblique stretching machine used for the solution casting described above may be preferably used for stretching and contracting of the film. The stretching temperature is preferably within the range of Tg to Tg+60° C. of a typical resin in the film.

Prior to reeling of the film, the edge portions of the film may be trimmed to a predetermined width conforming to product specification. The trimmed edges may be knurled (embossed) to prevent adhesion and scratching of the film during reeling. The film is knurled with a metal ring having an embossed pattern on the side face through heating and pressing. The edge portions of the film clamped with clips, which are usually deformed and unsuitable for products, are cut off. The cutoffs are reused in the film formation processes described above.

Retarder films according to the present invention are laminated such that the angle between the slow axis and the transmission or absorption axis of the polarizer element descried below intersect at substantially 45°, to produce a circularly polarizing plate. In the present invention, the term "substantially 45°" refers to an angle within the range of 40 to 50°.

The in-plane slow axis of the retarder film according to the present invention intersects the transmission or absorption axis of the polarizer element at an angle preferably within the range of 41 to 49°, more preferably 42 to 48°, more preferably 43 to 47°, most preferably 44 to 46°.

<<Circularly Polarizing Plate>>

The circularly polarizing plate according to the present invention should be produced through the cutting of a long roll of a laminate of a long protective film, a long polarizer element, and a long retarder film according to the present invention, stacked in this order. The circularly polarizing plate according to the present invention, which is composed of the retarder film according to the present invention, is included in an organic EL display device, which is described below, so as to block mirror reflection of metal electrodes in the organic EL elements in all wavelengths in the visible light range. This can prevent the reflection during viewing and enhance black display.

The circularly polarizing plate according to the present invention should have UV absorptive capacity. A protective film having UV absorptive capacity on the viewing side is preferred for the protection of both polarizer elements and organic EL elements from ultraviolet rays. A retarder film having UV absorptive capacity disposed on the light-emitting side (for example, the side adjacent to the organic EL elements) can reduce degradation of the organic EL elements in the organic EL display device described below.

The circularly polarizing plate according to the present invention includes a retarder film according to the present invention having a slow axis tilted from the longitudinal direction by an angle (i.e., orientation angle θ) of "substantially 45°." In this way, formation of an adhesive layer and bonding of the polarizer element and the retarder film can be carried out in a continuous production line. Specifically, a step of bonding the polarizer element and the retarder film can be incorporated into or after the step of drying, which is carried out subsequent to the step of producing the polarizer element through stretching of a polarizing film, to sequentially supply the polarizer element and the retarder film. The bonded polarizer element and retarder film can be reeled into a roll. In this way, the process can proceed to the subsequent step in a continuous online production line. During the bonding of the polarizer element and the retarder film, a protective film can also be fed from a roll and continuously bonded to the polarizer element and the retarder film. The retarder film and the protective film are preferably simultaneously bonded to the polarizer element, in view of high performance and productivity. That is, the protective film and the retarder film can be bonded to the opposite sides of the polarizer element during or after drying performed subsequent to the production of the polarizer element through stretching of a polarizing film, to produce a roll of circularly polarizing plate.

In the circularly polarizing plate according to the present invention, the polarizer element is preferably disposed between the retarder film according to the present invention and the protective film, and a cured layer is preferably laminated to the viewing side of the protective film.

The present invention is characterized in that the circularly polarizing plate according to the present invention is provided in an organic electroluminescent display device. The circularly polarizing plate according to the present invention in an organic electroluminescent display device prevents mirror reflection of metal electrodes of organic electroluminescent emitting bodies.

(Protective Film)

In a circularly polarizing plate according to the present invention, a polarizer element is preferably disposed between an optical film (retarder film) and a protective film. A film containing cellulose ester is suitable as a protective film for such a circularly polarizing plate. Preferred cellulose ester films are commercially available (for example, Konica Minolta TAC films KC8UX, KC5UX, KC4UX, KC8UCR3, KC4SR, KC4BR, KC4CR, KC4DR, KC4FR, KC4KR, KC8UY, KC6UY, KC4UY, KC4UE, KC8UE, KC8UY-HA, KC2UA, KC4UA, KC6UAKC, 2UAH, KC4UAH, and KC6UAH (which are products of Konica Minolta, Inc.), and Fuji TAC films T40UZ, T60UZ, T80UZ, TD80UL, TD60UL, TD40UL, R02, and ROE (which are product of Fujifilm Holdings Corporation)). The protective film may have any thickness. A typical thickness of a protective film is within the range of approximately 10 to 200 μm, preferably 10 to 100 μm, more preferably 10 to 70 μm.

(Polarizer Element)

A polarizer element transmits light polarized in a specific direction. An example of such a polarizer element includes polyvinyl alcohol polarizing films. Polyvinyl alcohol polarizing films are composed of polyvinyl alcohol films dyed with iodine or dichroic dyes.

To compose a polarizer element, a polyvinyl alcohol film is dyed after uniaxial stretching or uniaxially stretched after dying. The resulting film is preferably treated with a boron compound to enhance durability. The polarizer element preferably has a thickness within the range of 5 to 30 μm, more preferably 5 to 15 μm.

Preferred examples of polyvinyl alcohol films include the ethylene modified polyvinyl alcohol films disclosed in JP-A Nos. 2003-248123 and 2003-342322, which have an ethylene unit content of 1 to 4 mol %, a degree of polymerization of 2,000 to 4,000, and a degree of saponification of 99.0 to 99.99 mol %. A polarizer element, which is prepared in accordance with any of the procedures described in JP-A No. 2011-100161 and Japanese Patent Publication Nos. 4691205 and 4804589, should be bonded to an optical film according to the present invention to produce a polarizer.

(Adhesive)

Any bonding scheme may be used to bond the optical film and the polarizer element according to the present invention. An example bonding scheme involves bonding of a saponified optical film according to the present invention with a completely saponified polyvinyl alcohol adhesive. Although an active-beam curable adhesive is acceptable, light curable adhesive is preferred for the high elasticity of the resulting adhesive layer and a small degree of deformation in the polarizer.

A preferred example of a light curable adhesive is disclosed in JP-A No. 2011-028234, which has a composition containing the following components: (α) a cationically polymerizable compound; (β) a photocationic polymerization initiator; (γ) a photosensitizer having a maximum absorption wavelength of 380 nm or larger; and (δ) a naphthalene photosensitizer. Alternatively, other light curable adhesives may be used.

An example method of producing a polarizer with a light curable adhesive will now be described.

A polarizing plate can be produced through a method including:

(1) preprocessing step of treating a surface of a polarizer element of an optical film to enhance adhesiveness;

(2) an adhesive applying step of applying the light curable adhesive to at least one of adhesive surfaces of the polarizer element and the optical film;

(3) a bonding step of bonding the polarizer element and the optical film with an adhesive layer; and (4) a curing step of curing the adhesive layer disposed between the bonded polarizer element and optical film. The preprocessing step (1) is optional.

<1: Preprocessing Step>

In the preprocessing step, the surface of the optical film adjacent to the polarizer element is treated to enhance its adhesiveness. If optical films are bonded to both sides of the polarizer element, the surfaces of the optical films adjacent to the polarizer element should be treated to enhance their adhesiveness. Examples of adhesiveness enhancement treatment include corona treatment and plasma treatment.

<Adhesive Applying Step>

In the adhesive applying step, the light curable adhesive is applied to at least one of the bonding surfaces of the polarizer element and optical film. The light curable adhesive can be directly applied to the surface of the polarizer element and/or optical film through any application procedure. For example, various application tool may be employed, such as a doctor blade, a wire bar, a die coater, a comma coater, or a gravure coater. Alternatively, the light curable adhesive may be cast between the polarizer element and the optical film, and the adhesive may be uniformly spread through pressing with rollers.

<Bonding Step>

After the light curable adhesive is applied, the layers are to be bonded. In the bonding step, if the light curable adhesive is applied to the surface of the polarizer element in the previous applying step, the optical film is disposed over the adhesive. If the light curable adhesive is applied to a surface of the optical film in the applying step, the polarizer element is disposed over the adhesive. Alternatively, if the light curable adhesive is cast between the polarizer element and the optical film, the polarizer element and the optical film are layered on each other in their states. If optical films are bonded to both sides of a polarizer element with a light curable adhesive, the optical films are disposed onto both sides of the polarizer element with the applied light curable adhesive therebetween. Usually, the laminate of layers are pressed with rollers from both sides (i.e., the rollers press on the polarizer element and the optical film if the laminate contains an optical film bonded to a single side of a polarizer element, or the rollers press on the optical films if optical films are bonded to both sides of the polarizer element). Materials suitable for the rollers include metal and rubber. The opposing rollers may be composed of the same material or different materials.

<Curing Step>

In the curing step, the uncured light curable adhesive is irradiated with active energy beams to form a cured adhesive layer containing epoxy compounds and/or oxetane compounds. This process bonds the polarizer element and the optical film with the light curable adhesive. If an optical film is bonded to a single side of the polarizer element, the active energy beams may be radiated onto either the polarizer element or the optical film. Alternatively, if optical films are bonded to both sides of the polarizer element, one of the optical films bonded to both sides of the polarizer element with the light curable adhesive should be irradiated with active energy beams so as to simultaneously cure the layers of light curable adhesive applied on both sides.

Examples of active energy beams include visible light beams, ultraviolet light beams, X-rays, and electron beams. Electron beams and ultraviolet light beams are usually preferred for ready handling and sufficient curing rates.

Any condition on electron beam irradiation may be employed for the curing of the adhesive. For example, an electron beam is irradiated with an acceleration voltage preferably in the range of 5 to 300 kV, more preferably 10 to 250 kV. Electron beams having an acceleration voltage of 5 kV or more reaches the adhesive and achieves a desire degree of curing, whereas electron beams having an acceleration voltage of 300 kV or less has an optimal penetration and penetrates the transparent optical film and polarizer element without causing their damage. Typical dose is within the range of 5 to 100 kGy, preferably 10 to 75 kGy. A dose of 5 kGy or more achieves sufficient curing of the adhesive, whereas a dose of 100 kGy or less does not damage the transparent optical film and polarizer element. This prevents a reduction in mechanical strength and yellowing, achieving desired optical characteristics.

Any condition on the ultraviolet irradiation may be employed for the curing of the adhesive. The cumulative dose of the ultraviolet irradiation is preferably within the range of 50 to 1,500 mJ/cm$^2$, more preferably 100 to 500 mJ/cm$^2$.

In a polarizer prepared as described above, the adhesive may be provided at any thickness. A typical thickness is within the range of 0.01 to 10 μm, preferably 0.5 to 5.0 μm.

<<Organic EL Display Device>>

The organic EL display device according to the present invention includes a circularly polarizing plate according to the present invention as described above.

Specifically, the organic EL display device according to the present invention includes a circularly polarizing plate composed of an optical film (retarder film) according to the present invention and an organic EL element. Thus, the organic EL display device can prevent reflection of external light during viewing and improve the black display. The screen of the organic EL display device may have any size, for example, 20 inches or larger (1 inch designates 2.54 cm).

Figure 7:
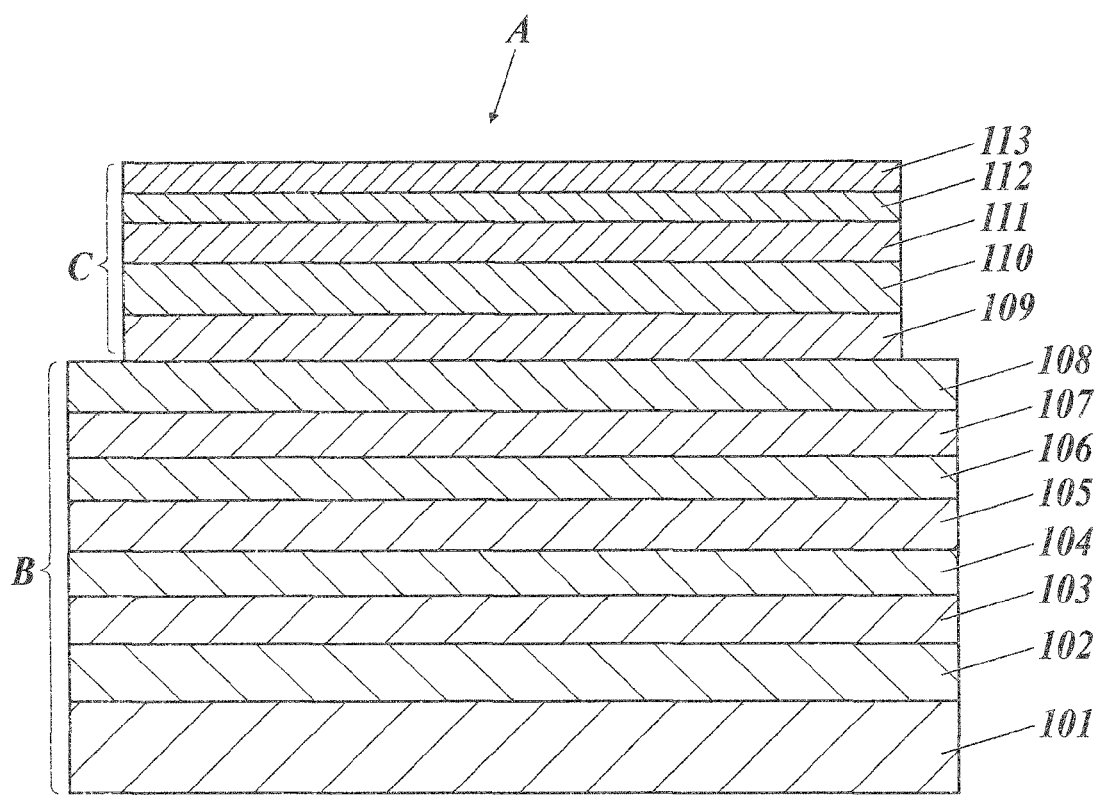
FIG. 7 is a schematic cross-sectional view showing an example of a configuration of an organic electroluminescent display device of the present invention.

FIG. 7 is a schematic view of an organic EL display device according to the present invention. The configuration of an organic EL display device A according to the present invention should not be limited to that illustrated in FIG. 7.

As shown in FIG. 7, the organic EL display device A includes an organic EL element B and a long circular polarizer C according to the present invention disposed on the organic EL device B; the organic EL device B includes a glass or polyimide transparent substrate 101, a metal electrode 102, a TFT 103, an organic functional layer unit 104, a transparent electrode (composed of ITO, for example) 105, an insulating layer 106, a sealing layer 107, and a film 108 (optional), disposed in sequence, and the circularly polarizing plate C includes a retarder film 109 according to the present invention, a protective film 111, and a polarizer element 110 disposed therebetween. A cured layer 112 is preferably disposed on the protective film 111. The cured layer 112 not only prevents the surface of the organic EL display device from scratches but also prevents bending due to the long circularly polarizing plate. An antireflective layer 113 may be disposed on the cured layer 112. The aforesaid organic EL element itself has a thickness of approximately 1.0 μm.

Typically, the organic EL display device includes a light-emitting element (organic EL element), which includes a transparent substrate, a metal electrode 102, an organic functional layer unit 104, and a transparent electrode 105, disposed in sequence. The organic functional layer unit 104 is a laminate of various thin-film organic functional layers. Examples of such laminates include a laminate of a hole injection layer, which is composed of a triphenylamine derivative, and a light-emitting layer, which is composed of a fluorescent organic solid, such as anthracene; a laminate of the above-mentioned light-emitting layer and an electron injection layer, which is composed of a perylene derivative; a laminate of a hole injection layer, a light-emitting layer, and an electron injection layer; and a laminate composed of a combination of the laminates mentioned above.

The principle of light emission in the organic EL display device involves applying a voltage to the transparent electrode 105 and the metal electrode 102, injecting holes and electrons to the organic functional layer unit 104, exciting phosphors with the energy generated through recombination of the holes and the electrons, and radiating light from the phosphors returning to the ground state. A typical diode is also based on the same mechanism of recombination. As presumed from this fact, an electric current and the intensity of emitted light exhibit high non-linearity with rectification against the applied voltage.

At least one of the electrodes in the organic EL display device A must be transparent in order to radiate the light generated in the organic functional layer unit 104. Thus, the organic EL display device usually includes a transparent electrode composed of a transparent conductor, such as indium tin oxide (ITO), serving as an anode. In contrast, the cathode should be composed of a substance having a small work function so as to facilitate electron injection and enhance the light-emitting efficiency. Thus, the organic EL display device usually includes a metal electrode composed of Mg—Ag or Al—Li, for example.

The circularly polarizing plate including the retarder film according to the present invention can be suitably used for a large-screen organic EL display device having a screen size of 20 inches or more, which is equivalent to a diagonal screen length of 50.8 cm or more.

The organic functional layer unit 104 including a light0emitting later in the organic EL display device A having such a configuration has a thickness of approximately 10 nm, which is significantly thin. Thus, the organic functional layer unit 104 is substantially transparent to light, like a transparent electrode 105. As a result, external light enters the surface of the transparent substrate in a non-light emitting mode, pass through the transparent electrode 105 and the organic functional layer unit 104, is reflected at the metal electrode 102, and returns to the surface of the transparent substrate. Thus, the screen of the organic EL display device appears as a mirror surface when viewed from outside.

An organic EL display device A includes an organic EL element having a transparent electrode 105 emitting light in response to application of a voltage on the front surface of an organic light-emitting layer unit 104 and a metal electrode 102 on the back surface of the organic light-emitting layer unit 104, and may further include a polarizing plate disposed on the front surface (viewed surface) of the transparent electrode 105 and a retarder disposed between the transparent electrode 105 and the polarizer C.

The retarder film and the polarizing plate have a function of polarizing incident external light reflected at the metal electrode. Thus, the polarizing effect causes the mirror surface of the metal electrode to appear externally invisible. Specifically, the retarder film is composed of a λ/4 retarder film, and the angle between the polarizing direction of the polarizer element and the polarizing direction of the retarder film is adjusted to 45° or 135°, so as to completely block light from the mirror surface of the metal electrode.

That is, only the linearly polarized component of the external light is incident on the organic EL display device through the polarizer element. This linearly polarized light is usually elliptically-polarized by the retarder but is circularly polarized if the retarder film is a λ/4 retarder film and the angle between the polarizing direction of the polarizer element and the polarizing direction of the retarder film to 45° or 135°.

The circularly polarized light transmits the transparent substrate, the transparent electrode, and the organic thin-film, is reflected at the metal electrode, transmits the organic thin-film, the transparent electrode, and the transparent substrate, and is linearly polarized at the retarder film. The linearly polarized light cannot transmit the polarizing plate because it is orthogonal to the polarization direction of the polarizing plate. As a result, the light from the mirror surface of the metal electrode is completely blocked.

EXAMPLES

Examples of the present invention will now be described in detail by referring to specific examples. The present invention will not be limited by these examples. The sign "%" in the examples refers to "mass %," unless otherwise specified. The degree of substitution and the number of substituents are an average value.

Example 1

<<Production of Retarder Film>>
[Production of Retarder Film A1]
(Preparation of Particle Dispersion)

| | |
|---|---|
| Particles (Aerosil R812 manufactured by Nippon Aerosil Co., Ltd.)) | 11 mass parts |
| Ethanol | 89 mass parts |

The particles and ethanol were mixed by agitation in a dissolver for 50 minutes and dispersed with a Manton-Gaulin disperser (manufactured by Gaulin Inc.), which is an ultrahigh-pressure homogenizer, to prepare a particle dispersion.
(Preparation of Particle Solution 1)

50 mass parts of dimethyl chloride were placed in a dissolving tank, and 50 mass parts of the particle dispersion were slowly added to the dimethyl chloride while sufficiently stirring the dimethyl chloride. The mixture was dispersed in an S type attritor to yield secondary particles having a predetermined particle size. This was filtered through Fine Met NF, manufactured by Nippon Seisen Co., Ltd., to prepare a particle solution 1.
(Preparation of Dope)

Dimethyl chloride and ethanol were placed in a pressure dissolving tank at quantities listed below. A cellulose derivative b1 synthesized as described above (the detail is described in Table 2) was added to the organic solvent in the pressure dissolving tank with stirring. The mixture was heated and stirred until completely dissolved. After addition of an additive (exemplary compound (1-1) and the particle solution 1, the solution was filtered through Azumi filter paper No. 244 manufactured by Azumi Filter Paper Co., Ltd., to prepared a dope.
<Composition of Dope>

| | |
|---|---|
| Dimethyl chloride | 340 mass parts |
| Ethanol | 64 mass parts |
| Cellulose derivative b1: benzolyl modified cellulose ester (substitution degree of the substituent (benzoate) having a multiple bond: 0.73; substitution degree of acetyl group: 2.15; total substitution degree: 2.88) | 100 mass parts |
| Additive: Exemplary compound 1-1 of Formula (1) | 5 mass parts |
| Particle solution 1 | 2 mass parts |

(Film Formation)

The prepared dope was cast onto a stainless steel endless belt, and then, the cast dope was separated from the stainless steel belt to obtain a material film.

The separated material film was unidirectionally stretched in the transverse direction (TD) with a tenter while heated. The conveying tension was adjusted to prevent contraction of the material film in the machine direction (MD).

Subsequently, the material film was conveyed through a drying zone by multiple rollers. The drying was finished. The dried film in a roll shape was produced.

(Stretching Step)

The material film was obliquely stretched with the diagonal stretching machine illustrated in FIG. 4 such that the optical slow axis of the film intersects the conveying direction at 45°, to produce a roll of retarder film A1.

The stretching conditions including the thickness, stretching temperature, and stretching rates in the transverse direction (TD) and machine direction (MD) of the material film were appropriately adjusted such that the in-plane retardation $Ro_{550}$ measured at a wavelength of 550 nm was 140 nm, the film thickness was 50 μm, and the ratio $Ro_{450}/Ro_{550}$ was 0.80.

[Production of Retarder Films A2 to A33]

Retarder films A2 to A33 were produced as in retarder film A1, except that cellulose derivatives and additives (compounds represented by Formula (1) and comparative compounds) were changed as combinations described in Table 3.

For Retarder films A2 to A10, and A14 to A30, the stretching conditions including the thickness, stretching temperature, and stretching rates in the transverse direction (TD) and machine direction (MD) of the material film were appropriately adjusted such that the in-plane retardation $Ro_{550}$ measured at a wavelength of 550 nm was 140 nm, the film thickness was 50 μm, and $Ro_{450}/Ro_{550}$ was the value listed in Table 3.

For Retarder films A11 to A13, A31 and A33, the stretching conditions including the thickness, stretching temperature, and stretching rates in the transverse direction (TD) and machine direction (MD) of the material film were appropriately adjusted such that the film thickness was 50 μm, and the in-plane retardation $Ro_{550}$ measured at a wavelength of 550 nm, and $Ro_{450}/Ro_{550}$ were the value listed in Table 3

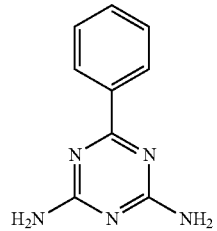

Comparative compound 1

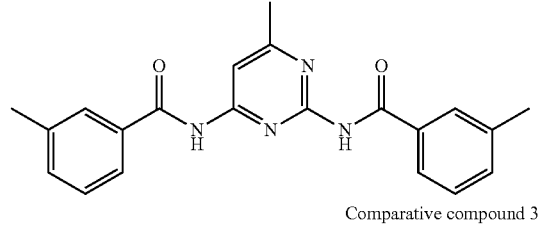

Comparative compound 2

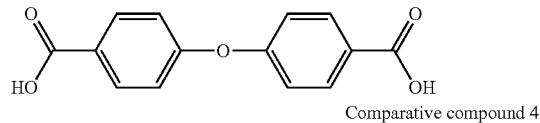

Comparative compound 3

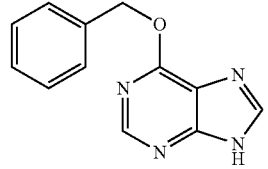

Comparative compound 4

The details of the cellulose derivatives each described in Table 3 are as follows.

Cellulose derivative b1: benzoyl modified cellulose ester (substitution degree of the substituent (benzoate) having multiple bonds; 0.73, substitution degree of acetyl group; 2.15, total substitution degree; 2.88)

Cellulose derivative b2: benzoyl modified cellulose ester (substitution degree of the substituent (benzoate) having multiple bonds; 0.93, substitution degree of methoxy group; 1.80, total substitution degree; 2.73)

Cellulose derivative b3: benzoyl modified cellulose ester (substitution degree of the substituent (benzoate) having multiple bonds; 0.55, substitution degree of ethoxy group; 2.30, total substitution degree; 2.85)

Cellulose derivative t1: thiophene carbonyl modified cellulose ester (substitution degree of the substituent (thiophene-2-carbonyl) having multiple bonds; 0.22, substitution degree of acetyl group; 2.15, total substitution degree; 2.37)

Cellulose derivative t2: thiophene carbonyl modified cellulose ester (substitution degree of the substituent (thiophene-2-carbonyl) having multiple bonds; 0.48, substitution degree of methoxy group; 1.80, total substitution degree; 2.28)

Cellulose derivative t3: thiophene carbonyl modified cellulose ester (substitution degree of the substituent (thiophene-2-carbonyl) having multiple bonds; 0.35, substitution degree of ethoxy group; 2.30, total substitution degree; 2.65)

Cellulose derivative p1: nicotinoyl modified cellulose ester (substitution degree of the substituent (nicotinoyl) having multiple bonds; 0.42, substitution degree of acetyl group; 2.15, total substitution degree; 2.57)

Cellulose derivative p2: isonicotinoyl modified cellulose ester (substitution degree of the substituent (isonicotinoyl) having multiple bonds; 0.50, substitution degree of methoxy group; 1.80, total substitution degree; 2.30)

Cellulose derivative m1: propionyl/benzoyl modified cellulose ester (substitution degree of the substituents having multiple bonds (propionyl: 0.50, benzoyl: 0.55); 1.05; substitution degree of methoxy group; 1.80, total substitution degree; 2.85)

Cellulose derivative m2: propionyl/benzoyl modified cellulose ester (substitution degree of the substituents having multiple bonds (propionyl: 0.22, thiophene carbonyl: 0.40); 0.62; substitution degree of ethoxy group; 2.30, total substitution degree; 2.92)

The values of (na−nb) of the compounds represented by Formula (1) and comparative compounds each were calculated by using Gaussian 03 (Revision B.03, software made by Gaussian Inc.). The value na was calculated by using the structure optimized with B3LYP/6-31G* level. The obtained polarizability tensor was diagonalized, then, the value was calculated from the diagonalized component. Among the eigenvalues obtained after diagonalization of the polarizability tensor, the maximum component is $\alpha_a$, the second largest component is $\alpha_b$, and the minimum component is $\alpha_c$. The van der Waals volume was also calculated starting from the structure optimized with B3LYP/6-31G* level.

From the measured polarizabilities $\alpha_a$, $\alpha_b$, and $\alpha_c$, and the van der Waals volume as described above, the refractive index was calculated from the formulas [Scheme 1] and [Scheme 2] as described above. Thus, the refractive index $n_a$ of the long axis direction of the compound A and refractive index $n_a$ of the orthogonal direction to the long axis direction of the compound A were obtained, and (na−nb) was calculated.

<<Production of Circularly Polarizing Plate>>

A polyvinyl alcohol film having a thickness of 120 μm was unidirectionally stretched at a temperature of 110° C. and a stretching rate of 5 times. The stretched film was dipped in a solution containing iodine (0.075 g), potassium iodide (5 g), and water (100 g) for 60 seconds, and then dipped in a solution containing potassium iodide (6 g), boric acid (7.5 g), and water (100 g) at 68° C. The film was washed with water and dried, to obtain a polarizer element.

Each retarder film produced in the process described above was bonded to the polarizer element with an adhesive such that the slow axis of the retarder film intersects the absorption axis of the polarizer element at 45°, and a protective film (Konica Minolta TAC film KC4UY having a thickness of 40 μm manufactured by Konica Minolta, Inc.) was bonded to the back side of the polarizer element with a liquid adhesive, to produce circularly polarizing plates A1 to A33.

<<Production of Organic EL Cell>>

An organic EL cell having a configuration illustrated in FIG. 8 of JP-A No. 2010-20925 was produced from 3-mm thick alkali-free glass having a 50-inch (127-cm) size, in accordance with the procedures shown in an embodiment in JP-A No. 2010-20925.

<<Production of Organic EL Display Device)

An adhesive was applied to a surface of each retarder film of each circularly polarizing plate prepared above and bonded to the viewing side of the corresponding organic EL cell, to produce organic EL display devices A1 to A33.

<<Evaluation of Organic EL Display Device>>

The organic EL display devices prepared through the process described above were evaluated.

[Evaluation 1 on Stability Against Humidity: Evaluation of Stability of Black Tone]

A black image was displayed on each organic EL display device having an intensity of 1,000 Lx at 5 cm above the outermost surface of the organic EL display device, under a low humidity environment of 23° C. and 20% RH. Subsequently, a black image was displayed under a high humidity environment of 23° C. and 80% RH.

The tone of the black display of each organic EL display device was observed and compared under the two different environments described above by ten test participants from the front (0° to the plane normal) and a 40° oblique angle to the plane normal, so as to evaluate the effect of humidity on the black tone in accordance with the ranks described below. The stability of the black tone against humidity is allowable for use if the evaluation is Δ or higher.

⊚: nine or ten participants recognized no effect of humidity on the displayed black image ○: seven or eight participants recognized no effect of humidity on the displayed black image Δ: five or six participants recognized no effect of humidity on the displayed black image X: four or less participants recognized no effect of humidity on the displayed black image

[Evaluation 2 on Stability Against Humidity: Evaluation of Stability of Reflectivity]

Organic EL display devices for evaluation were produced as in the organic EL display device described above, except that red, blue, and green lines were drawn with felt pen markers (Magic Inks, registered trademark) to the visible surface of the prepared organic EL cell.

The visibility (reflectivity) of the red, blue, and green felt pen lines on the organic EL display devices having an intensity of 1,000 Lx at 5 cm above the outermost surface of the organic EL display device were evaluated under a low humidity environment of 23° C. and 20% RH. Subsequently, the visibility (reflectivity) of the felt pen lines were evaluated under a high humidity environment of 23° C. and 80% RH by ten test participants in accordance with the ranks described below. The stability of the reflectivity against humidity is allowable for use if the evaluation is Δ or higher. The term "reflectivity" refers to reflection of light at an organic EL cell inside the circularly polarizing plate, not reflection at the surface of the circularly polarizing plate.

⊚: nine or ten participants recognized no effect of humidity on the visibility of the felt pen lines ○: seven or eight participants recognized no effect of humidity on the visibility of the felt pen lines Δ: five or six participants recognized no effect of humidity on the visibility of the felt pen lines X: four or less participants recognized no effect of humidity on the visibility of the felt pen lines The obtained results are listed in Table 3.

tone and reflectivity. In contrast, an organic EL display device provided with an optical film comprising a comparative compound, which has the features outside the defined features of the present invention, exhibited significant humidity dependence for the properties.

TABLE 3

| | | | | Additive | | | | | | Evaluation of humidity | | |
| | | | | | Expression (a2) | Cellulose derivative | | | Expression (a1) | stability | | |
| *A | *B | *C | *D | Other additive | $n_a - n_b$ | No. | *1 | $Ro_{450}/Ro_{550}$ | $Ro_{550}$ | Stability of black tone | Stability of reflectivity | Remarks |
|---|---|---|---|---|---|---|---|---|---|---|---|---|
| A1 | A1 | A1 | 1-1 | — | 1.41 | b1 | 0.73 | 140 | 0.80 | 0.80 | ◎ | ◎ | *E |
| A2 | A2 | A2 | 1-1 | — | 1.41 | b2 | 0.93 | 140 | 0.82 | 0.70 | ◎ | ◎ | *E |
| A3 | A3 | A3 | 1-1 | — | 1.41 | t1 | 0.22 | 140 | 0.88 | 0.32 | ◎ | ○ | *E |
| A4 | A4 | A4 | 1-1 | — | 1.41 | t2 | 0.48 | 140 | 0.82 | 0.85 | ◎ | ◎ | *E |
| A5 | A5 | A5 | 1-1 | — | 1.41 | t3 | 0.35 | 140 | 0.78 | 0.80 | ○ | ◎ | *E |
| A6 | A6 | A6 | 1-1 | — | 1.41 | p1 | 0.42 | 140 | 0.85 | 0.60 | ◎ | ○ | *E |
| A7 | A7 | A7 | 1-1 | — | 1.41 | p3 | 0.35 | 140 | 0.81 | 0.62 | ○ | ◎ | *E |
| A8 | A8 | A8 | 1-1 | — | 1.41 | p4 | 0.45 | 140 | 0.82 | 0.66 | ○ | ◎ | *E |
| A9 | A9 | A9 | 1-1 | — | 1.41 | m1 | 1.05 | 140 | 0.83 | 0.95 | ◎ | ○ | *E |
| A10 | A10 | A10 | 1-1 | — | 1.41 | m2 | 0.62 | 140 | 0.80 | 0.51 | ○ | ○ | *E |
| A11 | A11 | A11 | 1-1 | — | 1.41 | b1 | 0.73 | 120 | 0.80 | 0.80 | ◎ | ◎ | *E |
| A12 | A12 | A12 | 1-1 | — | 1.41 | b1 | 0.73 | 130 | 0.80 | 0.80 | ◎ | ◎ | *E |
| A13 | A13 | A13 | 1-1 | — | 1.41 | b1 | 0.73 | 160 | 0.80 | 0.80 | ◎ | ◎ | *E |
| A14 | A14 | A14 | 1-1 | — | 1.41 | b1 | 0.73 | 140 | 0.67 | 0.80 | ◎ | ◎ | *E |
| A15 | A15 | A15 | 1-1 | — | 1.41 | b1 | 0.73 | 140 | 0.75 | 0.80 | ◎ | ◎ | *E |
| A16 | A16 | A16 | 1-1 | — | 1.41 | b1 | 0.73 | 140 | 0.97 | 0.80 | ◎ | ◎ | *E |
| A17 | A17 | A17 | 1-6 | — | 1.25 | b2 | 0.93 | 140 | 0.82 | 0.70 | ◎ | ◎ | *E |
| A18 | A18 | A18 | 1-6 | — | 1.25 | t3 | 0.35 | 140 | 0.78 | 0.80 | ○ | ◎ | *E |
| A19 | A19 | A19 | 1-7 | — | 1.25 | p1 | 0.42 | 140 | 0.85 | 0.60 | ◎ | ◎ | *E |
| A20 | A20 | A20 | 1-17 | — | 0.53 | t1 | 0.22 | 140 | 0.88 | 0.32 | ◎ | ○ | *E |
| A21 | A21 | A21 | 1-26 | — | 0.84 | m2 | 0.62 | 140 | 0.80 | 0.51 | ○ | ○ | *E |
| A22 | A22 | A22 | 1-31 | — | 1.56 | b1 | 0.73 | 140 | 0.80 | 0.70 | Δ | ○ | *E |
| A23 | A23 | A23 | 1-32 | — | 1.69 | b1 | 0.73 | 140 | 0.80 | 0.70 | Δ | Δ | *E |
| A24 | A24 | A24 | — | Comparative compound 1 | 0.26 | b3 | 0.55 | 140 | 0.90 | 0.23 | X | X | *F |
| A25 | A25 | A25 | — | Comparative compound 1 | 0.26 | t1 | 0.22 | 140 | 0.92 | 0.25 | X | X | *F |
| A26 | A26 | A26 | — | Comparative compound 1 | 0.26 | p2 | 0.50 | 140 | 0.95 | 0.22 | X | X | *F |
| A27 | A27 | A27 | — | Comparative compound 2 | 0.32 | b2 | 0.93 | 140 | 0.93 | 0.22 | X | X | *F |
| A28 | A28 | A28 | — | Comparative compound 2 | 0.56 | t3 | 0.35 | 140 | 0.90 | 0.25 | X | X | *F |
| A29 | A29 | A29 | — | Comparative compound 3 | 0.20 | b1 | 0.73 | 140 | 0.92 | 0.18 | X | X | *F |
| A30 | A30 | A30 | — | Comparative compound 4 | 0.20 | t1 | 0.22 | 140 | 0.93 | 0.29 | X | X | *F |
| A31 | A31 | A31 | — | Comparative compound 1 | 0.26 | b3 | 0.55 | 110 | 0.90 | 0.23 | X | X | *F |
| A32 | A32 | A32 | — | Comparative compound 1 | 0.26 | b3 | 0.55 | 170 | 0.90 | 0.23 | X | X | *F |
| A33 | A33 | A33 | — | Comparative compound 1 | 0.26 | b3 | 0.55 | 140 | 0.60 | 0.23 | X | X | *F |

*1: Average substitution degree of substituents having a multiple bond
*A: Organic EL display device No.
*B: Circularly polarizing plate No.
*C: Retardation film No.
*D: Formula (1), Exemplary compound
*E: Present invention
*F: Comparative example The results in Table 3 demonstrate that an organic EL display device according to the present invention including a circularly polarizing plate including a retarder film having a configuration according to the present invention has significantly stable black tone and reflectivity (visibility) compared to those of a comparative example, even under an environment with greatly varying humidity.

That is, an organic EL display device of the present invention, which is provided with an optical film comprising a compound represented by Formula (1) of the present invention as a retarder film, exhibited small change of black

INDUSTRIAL APPLICABILITY

An optical film of the present invention can give retardation in an amount of substantially λ/4. It exhibits a reduced variation in optical performance under variable humidity, and functions as a protective film for a polarizing plate. It is suitably applied to: a circularly polarizing plate including the optical film; and an organic electroluminescent display device including the circularly polarizing plate as an antireflective component.

| DESCRIPTION OF SYMBOLS | |
|---|---|
| 1: | Water adsorbing resin |
| 2: | Dipole-dipole interaction |
| 3: | Hydrogen bonding |
| 4: | Additive having no CH-π bonding |
| 5: | Compound A |
| 6: | CH-π interaction |
| C: | Cellulose fiber |
| SW: | Swelling |
| 11: | Stretching direction |
| 12: | Oblique stretching direction |
| 13: | Conveying direction |
| 14: | Slow axis |
| D1: | Feeding direction |
| D2: | Reeling direction |
| F: | Optical film |
| θi: | Bending angle (feeding angle) |
| Ci: | Co: Gripper |
| Ri: | Ro: Rail |
| Wo: | Width of film before stretching |
| W: | Width of film after stretching |
| 16: | Film feeder |
| 17: | Conveying-direction changer |
| 18: | Winder |
| 19: | Film former |
| A: | Organic electroluminescent display device |
| B: | Organic electroluminescent element |
| C: | Circularly polarizing plate |
| 101: | Transparent substrate |
| 102: | Metal electrode |
| 103: | TFT |
| 104: | Organic functional layer unit |
| 105: | Transparent electrode |
| 106: | Insulating layer |
| 107: | Sealing layer |
| 108: | Film |
| 109: | λ/4 retarder film |
| 110: | Polarizer element |
| 111: | Protective film |
| 112: | Cured layer |
| 113: | Antireflective layer |

The invention claimed is:

1. An optical film comprising a cellulose derivative having a glucose skeleton containing a substituent, the optical film having an in-plane retardation $Ro_{550}$ within a range of 120 to 160 nm measured at a wavelength of 550 nm under an atmosphere of a temperature of 23° C. and a relative humidity of 55%, and a ratio $Ro_{450}/Ro_{550}$ within a range of 0.65 to 0.99, $Ro_{450}/Ro_{550}$ being a ratio of an in-plane retardation $Ro_{450}$ measured at a wavelength of 450 nm to the in-plane retardation $Ro_{550}$ measured at a wavelength of 550 nm, wherein, the substituent of the glucose skeleton in the cellulose derivative satisfies the following requirements (a) and (b), and the optical film contains a compound A satisfying the following condition defined by an Expression (a1), requirement (a): a part of the substituent contained in the glucose skeleton of the cellulose derivative is a substituent having a multiple bond, and an average degree of substitution of the substituent having a multiple bond is within a range of 0.1 to 3.0 per glucose skeleton unit, requirement (b): a maximum absorption wavelength of the substituent having a multiple bond is within a range of 220 to 400 nm, $$(Sw-S) \geq 0.30, \qquad \text{Expression (a1):}$$

wherein S represents an orientation degree of the compound A in the optical film, and Sw represents an orientation degree of the compound A in the optical film in the presence of water.

2. The optical film described in claim 1, wherein the compound A satisfies the following condition defined by an Expression (a2), and the compound A contains a plurality of ring structures including a heterocyclic ring in a long axis of the compound A, $$0.50 \leq (na-nb) \leq 1.50, \qquad \text{Expression (a2):}$$

wherein $n_a$ represents a refractive index in a long axis direction of the compound A, and $n_b$ represents a refractive index in an orthogonal direction to the long axis direction of the compound A.

3. The optical film described in claim 1, wherein the compound A is a compound having a structure represented by the following Formula (1):

$$A_1\text{-}L_1\text{-}W_1\text{-}L_2\text{-}B\text{-}(L_3\text{-}W_2\text{-}L_4)_n\text{-}A_2 \qquad \text{Formula (1)}$$

wherein $A_1$ and $A_2$ each represent an alkyl group, a cycloalkyl group, an aromatic hydrocarbon ring or an aromatic heterocyclic ring, $L_1$, $L_2$, $L_3$ and $L_4$ each represent a single bond or a divalent linking group, $W_1$ and $W_2$ each represent an aromatic heterocyclic ring or an aliphatic heterocyclic ring, B represents an aromatic hydrocarbon ring, an aliphatic hydrocarbon ring, an aromatic heterocyclic ring or aliphatic heterocyclic ring, n represents an integer of 0 to 5, provided that when n is 2 or more, a plurality of $L_3$, $L_4$ and $W_2$ are the same or different.

4. The optical film described in claim 1, wherein the average degree of substitution of the substituent having a multiple bond is within the range of 0.2 to 3.0 per glucose skeleton unit.

5. The optical film described in claim 1, wherein the average degree of substitution of the substituent having a multiple bond at positions 2, 3, and 6 of the glucose skeleton satisfies the following Expression (1), $$0 < (\text{Average degree of substitution at position 2} + \text{Average degree of substitution at position 3}) - \text{Average degree of substitution at position 6}. \qquad \text{Expression (1):}$$

6. The optical film described in claim 1, wherein the maximum absorption wavelength of the substituent having a multiple bond is within a range of 220 to 300 nm.

7. The optical film described in claim 1, wherein the substituent having a multiple bond contains an aromatic ring.

8. The optical film described in claim 1, wherein the optical film has a thickness within a range of 20 to 60 μm.

9. The optical film described in claim 1, wherein the optical film is a long film having a slow axis in a direction of 40 to 50° with respect to a longitudinal direction of the optical film.

10. A circularly polarizing plate comprising the optical film described in claim 1 and a polarizer element bonded to the optical film.

11. An organic electroluminescent display device provided with the circularly polarizing plate described in claim 10.

* * * * *